United States Patent [19]
Petersen et al.

[11] Patent Number: 5,464,796
[45] Date of Patent: Nov. 7, 1995

[54] 7-ISOINDOLINYL-QUINOLONE-CARBOXYLIC ACID DERIVATIVES

[75] Inventors: Uwe Petersen, Leverkusen; Andreas Krebs, Odenthal; Thomas Schenke, Bergisch Gladbach; Franz Kunisch, Odenthal-Glöbusch; Thomas Philipps, Köln; Klaus Grohe, Odenthal; Klaus-Dieter Bremm, Wuppertal; Rainer Endermann, Wuppertal; Karl-Georg Metzger, Wuppertal; Ingo Haller, Wuppertal; Hans-Joachim Zeiler, Wuppertal, all of Germany

[73] Assignee: Bayer Aktiengesellschaft, Leverkusen, Germany

[21] Appl. No.: 896,955

[22] Filed: Jun. 11, 1992

[30] Foreign Application Priority Data

Jun. 22, 1991 [DE] Germany ............... 41 20 646.0

[51] Int. Cl.⁶ ................ C07D 215/38; A61K 31/47
[52] U.S. Cl. ........................... 514/312; 546/156
[58] Field of Search ................ 546/156; 514/312

[56] References Cited

FOREIGN PATENT DOCUMENTS

| | | |
|---|---|---|
| 0047005 | 3/1982 | European Pat. Off. . |
| 0131839 | 1/1985 | European Pat. Off. . |
| 0154780 | 9/1985 | European Pat. Off. . |
| 0153580 | 9/1985 | European Pat. Off. . |
| 0247464 | 12/1987 | European Pat. Off. . |
| 0343524 | 11/1989 | European Pat. Off. . |
| 0343560 | 11/1989 | European Pat. Off. . |
| 0391132 | 10/1990 | European Pat. Off. . |
| 0429304 | 5/1991 | European Pat. Off. . |
| 3420743 | 6/1984 | Germany . |

OTHER PUBLICATIONS

Derwent Abstract of Japanese 90 04 20, 1992.
Journal of Medicinal Chemistry, vol. 33, 1990, pp. 1645–1656.
Journal of the American Chemical Society, Aug. 2, 1978, pp. 5179–5185.
J. Org. Chem., vol. 43, No. 11, 1978, pp. 2164–2167.
J. Org. Chem., vol. 40, No. 1975, pp. 24–28.
Methoden Der Organischen Chemie, vol. E4, 1983, p. 144.
Protective Groups in Organic Chemistry, Plenum Press, London and and New York, 1973.
Tetrahedron, vol. 23, pp. 4719 to 4727, Pergamon Press Ltd., 1967.
Tetrahedron, Vel. 42, No. 11, pp. 2847–2853, 1986.
J. Org. Chem., vol. 39, No. 3 1974, pp. 319 to 321.

*Primary Examiner*—C. Warren Ivy
*Assistant Examiner*—D. Margaret M. Mach
*Attorney, Agent, or Firm*—Sprung Horn Kramer & Woods

[57] ABSTRACT

The invention relates to new quinolone- and naphthyridonecarboxylic acid derivatives which are substituted in the 7-position by a partly hydrogenated isoindolinyl ring, processes for their preparation and antibacterial agents and feed additives containing these compounds.

10 Claims, No Drawings

7-ISOINDOLINYL-QUINOLONE-CARBOXYLIC ACID DERIVATIVES

The invention relates to new quinolone- and naphthyridonecarboxylic acid derivatives which are substituted in the 7-position by a partially hydrogenated isoindolinyl ring, processes for their preparation and antibacterial agents and feed additives containing these compounds.

Quinolone- and naphthyridonecarboxylic acids which are substituted in the 7-position by an isoindolinyl ring, such as, for example, 7-(2-isoindolinyl)-1-cyclopropyl-6,8-difluoro-1,4-dihydro-4-oxo-3-quinolinecarboxylic acid, are already known from EP 343,560. However, these compounds are distinguished by only a low antibacterial activity.

It has been found that the compounds of the formula (I)

in which $X^1$ represents halogen, $X^2$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or methyl, $R^1$ represents alkyl having 1 to 4 carbon atoms, alkenyl having 2 to 4 carbon atoms, cycloalkyl having 3 to 6 carbon atoms, 2-hydroxyethyl, 2-fluoroethyl, methoxy, amino, methylamino, ethylamino, dimethylamino or phenyl which is optionally substituted by 1 or 2 fluorine atoms, $R^2$ represents hydrogen, alkyl having 1 to 4 carbon atoms which is optionally substituted by hydroxyl, methoxy, amino, methylamino or dimethylamino, or (5-methyl-2-oxo-1,3-dioxol-4-yl)-methyl, Z represents a radical having the structure wherein $R^4$ represents hydrogen, hydroxyl, hydroxy methyl or $$-CH_2-N\begin{matrix}R^3\\R^6\end{matrix},$$

wherein $R^3$ denotes hydrogen, optionally hydroxyl-substituted $C_1$–$C_3$-alkyl, alkoxycarbonyl having 1 to 4 C atoms in the alkoxy part or $C_1$–$C_3$-acyl and $R^6$ denotes hydrogen or methyl, $R^5$ represents hydrogen, $C_1$–$C_3$-alkyl or cyclopropyl, $R^{5'}$ represents hydrogen or methyl and A represents N or C—$R^7$, wherein $R^7$ represents H, halogen, methyl, hydroxyl or methoxy, or, together with $R^1$, can also form a bridge having the structure $$-O-CH_2-\overset{*}{CH}-CH_3,\quad -S-CH_2-\overset{*}{CH}-CH_3 \text{ or}$$

$$-CH_2-CH_2-\overset{*}{CH}-CH_3$$

and pharmaceutically usable hydrates and acid addition salts thereof as well as the alkali metal, alkaline earth metal, silver and guanidinium salts of the underlying carboxylic acids, have a higher antibacterial action, especially in the Gram-positive region, compared with the prior art. preferred compounds of the formula (I) are those in which $X^1$ represents fluorine, $X^2$ represents hydrogen, amino, methylamino, hydroxyl, methoxy, fluorine, chlorine, bromine or methyl, $R^1$ represents alkyl having 1 to 3 carbon atoms, vinyl, cycloalkyl having 3 or 4 carbon atoms, 2-fluoroethyl or phenyl which is optionally substituted by 1 or 2 fluorine atoms, $R^2$ represents hydrogen, alkyl having 1 or 2 carbon atoms which is optionally substituted by amino, methylamino or dimethylamino, or (5-methyl-2-oxo-1,3-dioxol-4-yl)-methyl, Z represents a radical having the structure wherein $R^4$ represents hydrogen, hydroxyl or $$-N\begin{matrix}R^3\\R^6\end{matrix},$$

wherein $R^3$ denotes hydrogen, optionally hydroxyl-substituted $C_1$–$C_2$-alkyl, alkoxycarbonyl having 1 to 4 C atoms in the alkoxy part or $C_1$–$C_3$-acyl and $R^6$ denotes hydrogen or methyl, $R^5$ represents hydrogen or methyl and A represents N or C—$R^7$, wherein $R^7$ represents H, fluorine, chlorine, bromine, methyl or methoxy, or, together with $R^1$, can also form a bridge having the structure $$-O-CH_2-\overset{*}{\underset{|}{CH}}-CH_3,$$

and pharmaceutically usable hydrates and acid addition salts thereof, as well as the alkali metal, alkaline earth metal, silver and guanidinium salts of the underlying carboxylic acids.

Particularly preferred compounds of the formula (I) are those in which $X^1$ represents fluorine, $X^2$ represents hydrogen, amino, fluorine, chlorine or bromine, $R^1$ represents alkyl having 1 or 2 carbon atoms, cyclopropyl or phenyl which is optionally substituted by 1 or 2 fluorine atoms, $R^2$ represents hydrogen or alkyl having 1 or 2 carbon atoms and Z represents a radical having the structure wherein $R^4$ represents hydrogen, hydroxyl or wherein $R^3$ denotes hydrogen, methyl, alkoxycarbonyl having 1 to 4 C atoms in the alkoxy part or $C_1$–$C_3$-acyl and $R^6$ denotes hydrogen or methyl, $R^5$ represents hydrogen or methyl and A represents N or C—$R^7$, wherein $R^7$ represents H, fluorine, chlorine or methoxy, or, together with $R^1$, can also form a bridge having the structure $$-O-CH_2-\overset{*}{\underset{|}{CH}}-CH_3,$$

and pharmaceutically usable hydrates and acid addition salts thereof, as well as the alkali metal, alkaline earth metal, silver and guanidinium salts of the underlying carboxylic acids.

It has furthermore been found that the compounds of the formula (I) are obtained by a process in which a compound of the formula (II)

in which

A, $R^1$, $R^2$, $X^1$ $X^2$ have the abovementioned meaning and $X^3$ represents halogen, in particular fluorine or chlorine, is reacted with compounds of the formula (III)

in which

Z has the abovementioned meaning, if appropriate in the presence of acid-trapping agents.

If, for example, 1-cyclopropyl-6,7,8-trifluoro-1,4-dihydro-4-oxo-3-quinolinecarboxylic acid and cis-7-methyl-4-methylamino-1,3,3a,4,7,7a-hexahydro-isoindole are used as starting substances, the course of the reaction can be represented by the following equation:

If, for example, ethyl 7-chloro-6-fluoro-1-(4-fluorophenyl)-1,4-dihydro-4-oxo-1,8-naphthyridine-3-carboxylate and 4-methylamino-1,3,3a,4,7,7a-hexahydroisoindole are used as starting substances, the course of the reaction can be represented by the following equation:

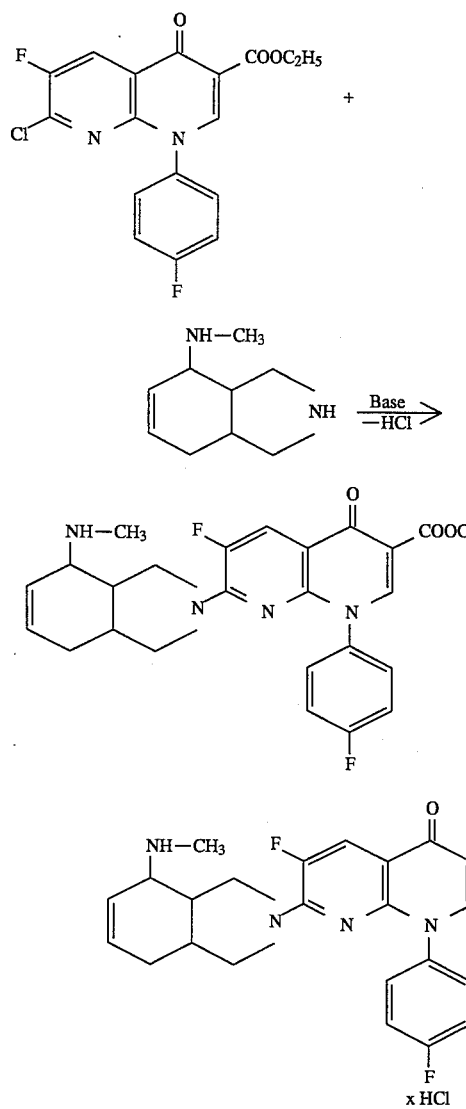

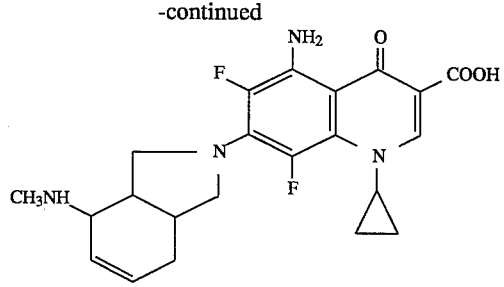

If, for example, 1-cyclopropyl-6-fluoro-1,4-dihydro-7-(cis-7-methyl-4 -methylamino-hexahydroisoindol-2-yl)-4-oxo-3-quinolinecarboxylic acid and ethanol/hydrogen chloride are used as starting substances, the course of the reaction can be represented by the following equation:

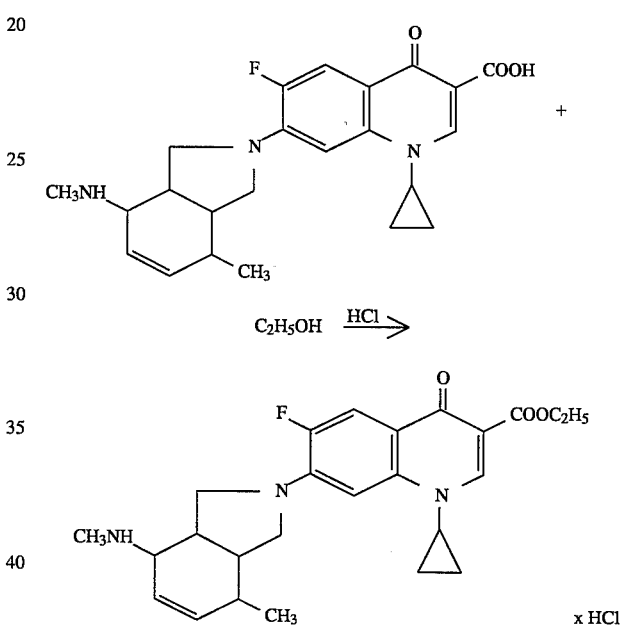

If, for example, 1-cyclopropyl-5,6,8-trifluoro-1,4-dihydro-7-(4-methylamino-1,3,3 a,4,7,7a-hexahydro-iso-indol-2-yl)-4-oxo-3-quinolinecarboxylic acid and ammonia are used as starting substances, the course of the reaction can be represented by the following equation:

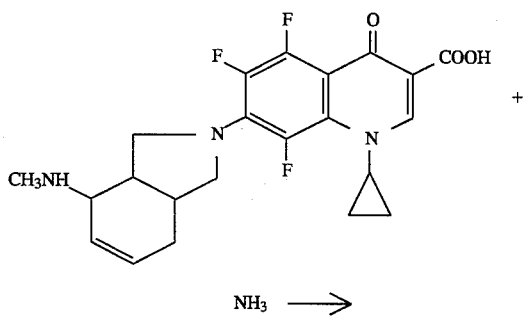

Most of the compounds of the formula (II) used as starting substances are known or can be prepared by known methods. Examples which may be mentioned are:
7-chloro-1-cyclopropyl-6-fluoro-1,4-dihydro-4-oxo-3-quinolinecarboxylic acid (German Patent Application 3,142,854),
1-cyclopropyl-6,7-difluoro-1,4-dihydro-4-oxo-3-quinolinecarboxylic acid (European Patent Application 113,091),
6-chloro-1-cyclopropyl-7,8-difluoro-1,4-dihydro-4-oxo-3-quinolinecarboxylic acid (German Patent Application 3,420,743),
8-chloro-1-cyclopropyl-6,7-difluoro-1,4-dihydro-4-oxo-3-quinolinecarboxylic acid (German Patent Application 3,420,743),
1-cyclopropyl-6,7,8-trifluoro-1,4-dihydro-4-oxo-3-quinolinecarboxylic acid (German Patent Application 3,318,145),
5-bromo-1-cyclopropyl-6,7,8-trifluoro-1,4-dihydro-4-oxo-3-quinolinecarboxylic acid,
5-bromo-1-(2,4-difluorophenyl)-6,7,8-trifluoro-1,4-dihydro-4-oxo-3-quinolinecarboxylic acid,
1-cyclopropyl-6,7-difluoro-1,4-dihydro-8-methyl-4-oxo-3-quinolinecarboxylic acid, 6,7-difluoro- 1-ethyl- 1,4 -dihydro-4 -oxo- 3 -quinolinecarboxylic acid, 7-chloro-6-fluoro- 1-ethyl- 1,4-dihydro-4 -oxo-3-quinolinecarboxylic acid, 7-chloro-6-fluoro-1,4-dihydro-1-(2-hydroxyethyl)-4-oxo-3-quinolinecarboxylic acid, 6,7-difluoro-1-(2-fluoroethyl)-1,4-dihydro-4-oxo-3-quinolinecarboxylic acid, 7-chloro-6-fluoro-1,4-dihydro-1-methoxy-4-oxo-3-quinolinecarboxylic acid, 7-chloro-6-fluoro-1,4-dihydro-1-methylamino-4-oxo-3-quinolinecarboxylic acid, 6,7-difluoro-1,4-dihydro-4-oxo-1-phenyl-3-quinolinecarboxylic acid, 7-chloro-1-cyclopropyl-6-fluoro-1,4-dihydro-4-oxo-1,8-naphthyridine-3-carboxylic acid, ethyl 7-chloro-1-cyclopropyl-6-fluoro-1,4-dihydro-4-oxo-1,8-naphthyridine-3-carboxylate, ethyl 1-cyclopropyl-6,7,8-trifluoro-1,4-dihydro-4-oxo-3-quinolinecarboxylate (German Patent Application 3,318, 145), 9,10-difluoro-2,3-dihydro-3-methyl-7-oxo-7H-pyrido-[1,2,3-de][1,4]benzoxacine-6 -carboxylic acid (European Patent Application 47,005), 8,9-difluoro-6,7-dihydro-5-methyl-1-oxo-1H,5H-benzo[i,j] quinolicine-2-carboxylic acid, 7-chloro-6-fluoro-1-phenyl-1,4-dihydro-4-oxo-1,8-naphthyridine-3-carboxylic acid (European Patent Application 153,580), ethyl 7-chloro-6-fluoro-1-(4-fluorophenyl)-1,4-dihydro-4-oxo-1,8-naphthyridine-3 -carboxylate 6,7,8-trifluoro-1,4-dihydro-1-methylamino-4-oxo-3-quinolinecarboxylic acid (German Patent Application 3,409, 922), 1-amino-6,7,8-trifluoro-1,4-dihydro-4-oxo-3-quinolinecarboxylic acid (German Patent Application 3,409,922), 6,7,8-trifluoro-1,4-dihydro-1-dimethylamino-4-oxo-3-quinolinecarboxylic acid (German Patent Application 3,409,922), 6,7-difluoro-1-(4-fluorophenyl)-1,4-dihydro-8-methyl-4-oxo-3-quinolinecarboxylic acid, 7-chloro-6-fluoro-1-(4-fluorophenyl)-1,4-dihydro-4-oxo-3-quinolinecarboxylic acid (European Patent Application 131,839), 7-chloro-6-fluoro-1-(2,4-difluorophenyl)-1,4-dihydro-4-oxo-3-quinolinecarboxylic acid (European Patent Application 131,839), 6,7,8-trifluoro-1-(4-fluorophenyl)-1,4-dihydro-4-oxo-3-quinolinecarboxylic acid (European Patent Application 154,780), 6,7,8-trifluoro-1-(2,4-difluorophenyl)-1,4-dihydro-4-oxo-3-quinolinecarboxylic acid (European Patent Application 154,780), 6,7,8-trifluoro-1,4-dihydro-4-oxo-1-phenyl-3-quinolinecarboxylic acid (European Patent Application 154,780), 7-chloro-1-ethyl-6-fluoro-1,4-dihydro-4-oxo-1,8-naphthyridine-3-carboxylic acid, 6,7-difluoro-1,4-dihydro-4-oxo-1-vinyl-3-quinolinecarboxylic acid, 1-cyclopropyl-5,6,7,8-tetrafluoro-1,4-dihydro-4-oxo-3-quinolinecarboxylic acid, 5-amino-1-cyclopropyl-6,7,8-trifluoro-1,4-dihydro-4-oxo-3-quinolinecarboxylic acid, 1-cyclopropyl-6,7,8-trifluoro-1,4-dihydro-5-hydroxy-4-oxo-3-quinolinecarboxylic acid, 1-cyclopropyl-6,7-difluoro-1,4-dihydro-8-methoxy-4-oxo-3-quinolinecarboxylic acid, 7-chloro-1-(2,4-difluorophenyl)-6-fluoro-1,4-dihydro-4-oxo-1,8-naphthyridine-3-carboxylic acid and ethyl 7-chloro-1-(2,4-difluorophenyl)-6-fluoro-1,4-dihydro-4-oxo-1,8-naphthyridine-3 -carboxylate.

The substituted 1,3,3a,4,7,7a-hexahydro-isoindoles of the formula (III) are mainly new. They can be obtained, for example, by a Dieis-Alder reaction of dienes of the formula (1)

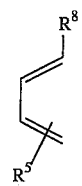

wherein $R^5$ has the abovementioned meaning and $R^8$ either is identical to $R^4$ or represents a functional group which can be converted into $R^4$, with dienophiles of the formula (2)

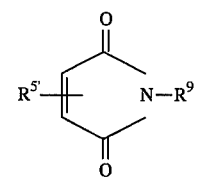

in which $R^9$ denotes hydrogen or a protective group, such as trimethylsilyl, benzyl, $C_1$–$C_4$-alkylphenylmethyl, methoxybenzyl or benzhydryl and $R^{5'}$ denotes hydrogen or methyl, and subsequent reduction of the carbonyl groups and if appropriate splitting off of the protective group.

Possible diluents for the Dieis-Alder reaction are all the inert organic solvents. These include, preferably, ethers, such as diisopropyl ether, di-n-butyl ether, dimethoxyethane, tetrahydrofuran and anisole, hydrocarbons, such as, for example, hexane, methylcyclohexane, toluene, xylene and mesitylene, and halogenated hydrocarbons, such as, for example, chloroform, 1,2-dichloroethane and chlorobenzene. However, the Dieis-Alder reaction can also be carried out without a solvent.

The reaction temperatures can be varied within a substantial range. The reaction is in general carried out between about −20° C. and +200° C., preferably between −20° C. and +150° C. The Dieis-Alder reaction is usually carried out under normal pressure. However, pressures up to 1.5 GPa can also be employed to accelerate the reaction.

The reduction of the carbonyl groups can be achieved with complex hydrides. Hydrides which can be employed are, for example, lithium aluminium hydride, lithium borohydride, lithium triethylborohydride, sodium bis-[2-methoxyethoxy]-aluminium hydride or sodium borohydride in the presence of Lewis acid catalysts, such as chlorotrimethylsilane, boron trifluoride etherate or aluminium chloride.

Diluents which can be used are the solvents customary for such reductions. These include, preferably, ethers, such as, for example, diethyl ether, tetrahydrofuran, dioxane or dimethoxyethane, and hydrocarbons, such as, for example, hexane, methylcyclohexane and toluene, or also mixtures thereof.

The reaction temperatures can be varied in the range between −40° and +180° C., preferably between 0° and 140° C. The reduction is in general carried out under normal pressure, but can also be carried out under reduced pressure or under increased pressure.

The use of pressures of between 100 and 1000 kPa is advisable in order to achieve higher reaction temperatures with low-boiling solvents.

The complex hydrides are employed at least in an amount corresponding to the stoichiometry of the reduction. However, an excess, preferably of between 30 and 300%, is in general employed.

Any protective group present is split off by the generally known methods of protective group chemistry (compare, for example, T. W. Greene, "Protective Groups in Organic Synthesis", John Wiley & Sons, New York 1981).

The starting substances of the formulae (1) and (2) are known or can be prepared by generally known methods of organic chemistry [compare, for example, J. Am. Chem. Soc. 100, 5179 (1978), J. Org. Chem. 43, 2164 (1978), DE 39 27 115, and J. Org. Chem. 40, 24 (1975)].

If, for example, 1-(tert.-butyloxycarbonylamino)-1,3-butadiene and maleimide are used as starting materials and lithium aluminium hydride is used as the reducing agent, the course of the reaction can be represented by the following equation:

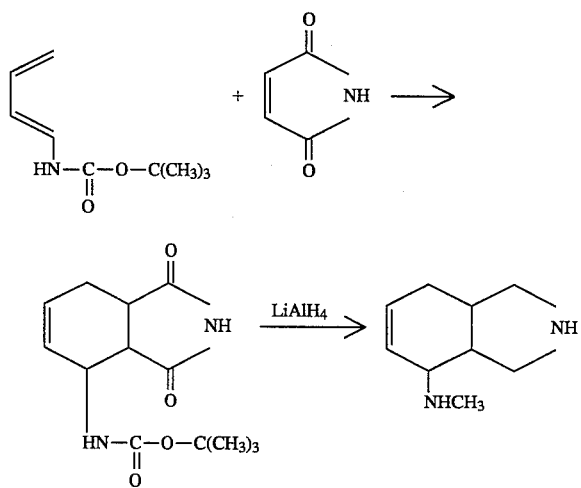

In a particular embodiment of the preparation process, all the stages can be carried out without isolation of the intermediate products if a suitable solvent is used, such as, for example, tetrahydrofuran. If, for example, 1-(tert.-butyloxycarbonylamino)-1,3-pentadiene and N-trimethylsilyl-maleimide are used as starting materials, the course of the reaction can be represented by the following equation:

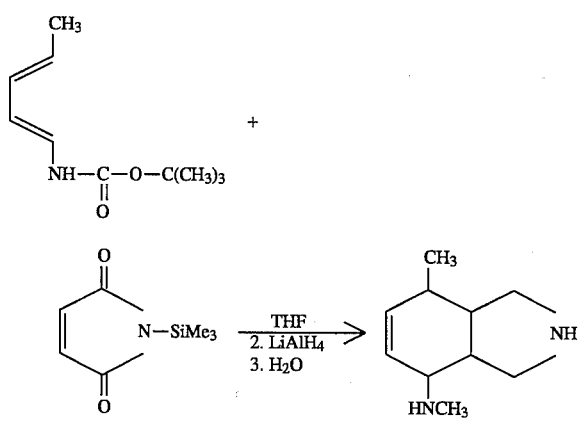

In this case, it can be demonstrated by NMR spectroscopy that all the substituents on the 6-membered ring have the cis-arrangement with respect to one another.

Examples which may be mentioned of compounds of the formula (III), which can be employed either as racemates or as enantiomerically or diastereomerically pure compounds, are:

4-amino-1,3,3a,4,7,7a-hexahydroisoindole,
4-methylamino-1,3,3a,4,7,7a-hexahydroisoindole,
5-methyl-4-methylamino-1,3,3a,4,7,7a-hexahydroisoindole,
6-methyl-4-methylamino-1,3,3a,4,7,7a-hexahydroisoindole,
7-methyl-4-methylamino-1,3,3a,4,7,7a-hexahydroisoindole,
7a-methyl-4-methylamino-1,3,3a,4,7,7a-hexahydroisoindole,
6,7-dimethyl-4-methylamino-1,3,3a,4,7,7a-hexahydroisoindole,
7-ethyl-4-methylamino-1,3,3a,4,7,7a-hexahydroisoindole,
7-isopropyl-4-methylamino-1,3,3a,4,7,7a-hexahydroisoindole,
4-methylamino-7-cyclopropyl-1,3,3a,4,7,7a-hexahydroisoindole,
4-dimethylamino-1,3,3a,4,7,7a-hexahydroisoindole,
4-ethylamino-1,3,3a,4,7,7a-hexahydroisoindole,
4-[(2-hydroxyethyl)-amino]-1,3,3a,4,7,7a-hexahydroisoindole,
4-[N-(2-hydroxyethyl)-N-methyl-amino]-1,3,3a,4,7,7a-hexahydroisoindole,
4-aminomethyl-1,3,3a,4,7,7a-hexahydroisoindole,
4-methylaminomethyl-1,3,3a,4,7,7a-hexahydroisoindole,
4-hydroxy-1,3,3a,4,7,7a-hexahydroisoindole and
4-hydroxymethyl-1,3,3a,4,7,7a-hexahydroisoindole.

The reaction of (II) with (III), in which the compounds (III) can also be employed in the form of their salts, such as, for example, the hydrochlorides, is preferably carried out in a diluent, such as dimethyl sulphoxide, N,N-dimethylformamide, N-methylpyrrolidone, hexamethylphosphoric triamide, sulpholane, acetonitrile, water, an alcohol, such as methanol, ethanol, n-propanol or isopropanol, glycol monomethyl ether or pyridine. Mixtures of these diluents can also be used.

Acid-binding agents which can be used are all the customary inorganic and organic acid-binding agents. These include, preferably, the alkali metal hydroxides, alkali metal carbonates, organic amines and amidines. Compounds which may be mentioned specifically as being particularly suitable are: triethylamine, 1,4-diazabicyclo[2.2.2]octane (DABCO), 1,8-diazabicyclo[5.4.0]undec-7-ene (DBU) or excess amine (III).

The reaction temperatures can be varied within a substantial range. The reaction is in general carried out between about 20° and 200° C., preferably between 80° and 180° C.

The reaction can be carried out under normal pressure, but also under increased pressure. It is in general carried out under pressures between about 1 and 100 bar, preferably between 1 and 10 bar.

In carrying out the process according to the invention, 1 to 15 mol, preferably 1 to 6 mol, of the compound (III) are employed per 1 mol of the compound (II).

Free amino groups can be protected by a suitable amino-protective group, for example by the tert.-butoxycarbonyl radical or as the azomethine group, during the reaction and can be liberated again by treatment with a suitable acid, such as hydrochloric acid or trifluoroacetic acid, when the reaction has ended (see Houben-Weyl, Methoden der Organischen Chemie (Methods of Organic Chemistry), Volume E4, page 144 (1983); and J. F. W. McOmie, Protective Groups in Organic Chemistry (1973), page 43).

To prepare the esters according to the invention, the underlying carboxylic acid is preferably reacted in excess alcohol in the presence of strong acids, such as sulphuric acid, anhydrous hydrogen chloride, methanesulphonic acid, p-toluenesulphonic acid or acid ion exchangers, at temperatures of about 20° to 200° C., preferably about 60° to 120° C. The water of reaction formed can also be removed by azeotropic distillation with chloroform, carbon tetrachloride, benzene or toluene.

Esters are also advantageously prepared by heating the underlying acid with dimethylformamide dialkyl acetate in a solvent, such as dimethylformamide.

The (5-methyl-2-oxo-1,3-dioxol-4-yl-methyl) esters used as prodrugs are obtained by reaction of an alkali metal salt of the underlying carboxylic acid, which can be protected on the N atom, if appropriate, by a protective group, such as the tert.-butoxycarbonyl radical, with 4-bromomethyl- or 4-chloromethyl-5-methyl-1,3-dioxol-2-one in a solvent, such as dimethylformamide, dimethylacetamide, N-methylpyrrolidone, dimethyl sulphoxide or tetramethylurea, at temperatures of about 0° to 100° C., preferably 0° to 50° C.

The acid addition salts of the compounds according to the invention are prepared in the customary manner, for example by dissolving the betaine in excess aqueous acid and precipitating the salt with a water-miscible organic solvent, such as methanol, ethanol, acetone or acetonitrile. It is also possible to heat equivalent amounts of betaine and acid in water or an alcohol, such as glycol monomethyl ether, and subsequently to evaporate the mixture to dryness or to filter off the precipitated salt with suction. Pharmaceutically usable salts are to be understood as, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

The alkali metal or alkaline earth metal salts of the carboxylic acids according to the invention are obtained, for example, by dissolving the betaine in less than the equivalent amount of alkali metal hydroxide solution or alkaline earth metal hydroxide solution, filtering off the undissolved betaine and evaporating the filtrate to dryness. Pharmaceutically suitable salts are the sodium, potassium or calcium salts. The corresponding silver salts are obtained by reaction of an alkali metal salt or alkaline earth metal salt with a suitable silver salt, such as silver nitrate.

Apart from the active compounds mentioned in the examples, the active compounds listed in the following table can also be prepared:

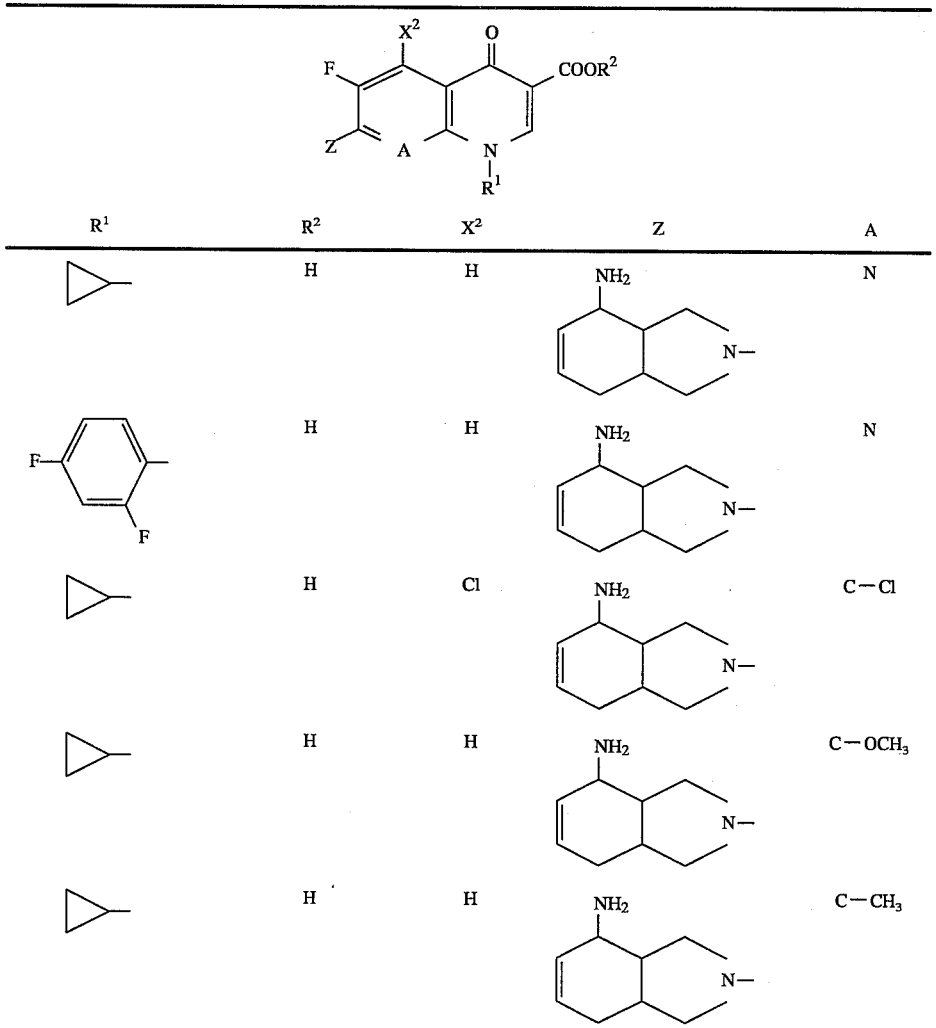

-continued
| R¹ | R² | X² | Z | A |
|---|---|---|---|---|
| 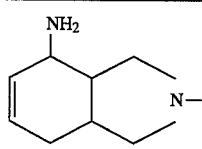 | H | CH₃ |  | CH |
| 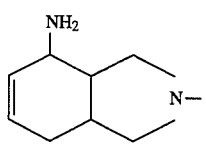 | H | CH₃ |  | CF |
| 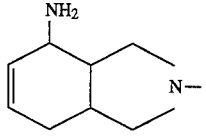 | H | H |  | C—Br |
| 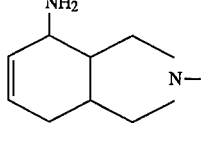 | H | Br | 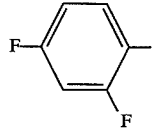 | CF |
| 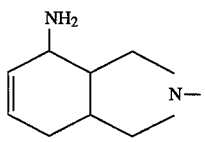 | H | Br |  | CF |
| 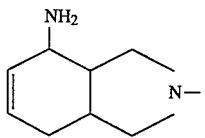 | H | F |  | CF |
| 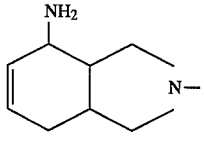 | H | F |  | CH |
| 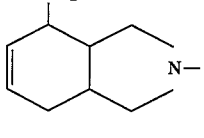 | C₂H₅ | H |  | CF |
| 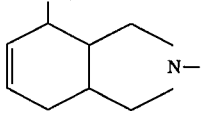 | CH₂CH₂NH₂ | H | | CF |

-continued
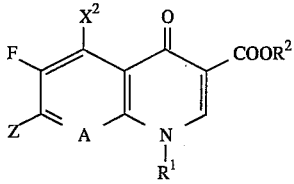
| $R^1$ | $R^2$ | $X^2$ | Z | A |
|---|---|---|---|---|
| cyclopropyl | $CH_2CH_2-OH$ | H |  | CCl |
| $C_2H_5$ | H | H | 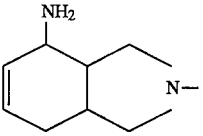 | CF |
| cyclopropyl | H | $NH_2$ | 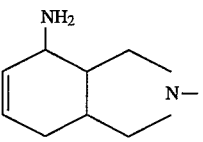 | CF |
| cyclopropyl | H | H |  | CF |
| cyclopropyl | H | H | 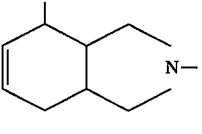 | CF |
| cyclopropyl | H | H |  | CF |
| cyclopropyl | H | H | 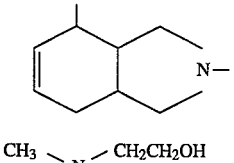 | CF |
| cyclopropyl | H | H |  | CF |
| cyclopropyl | H | H | 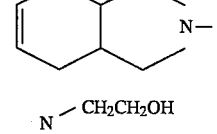 | CF |

-continued
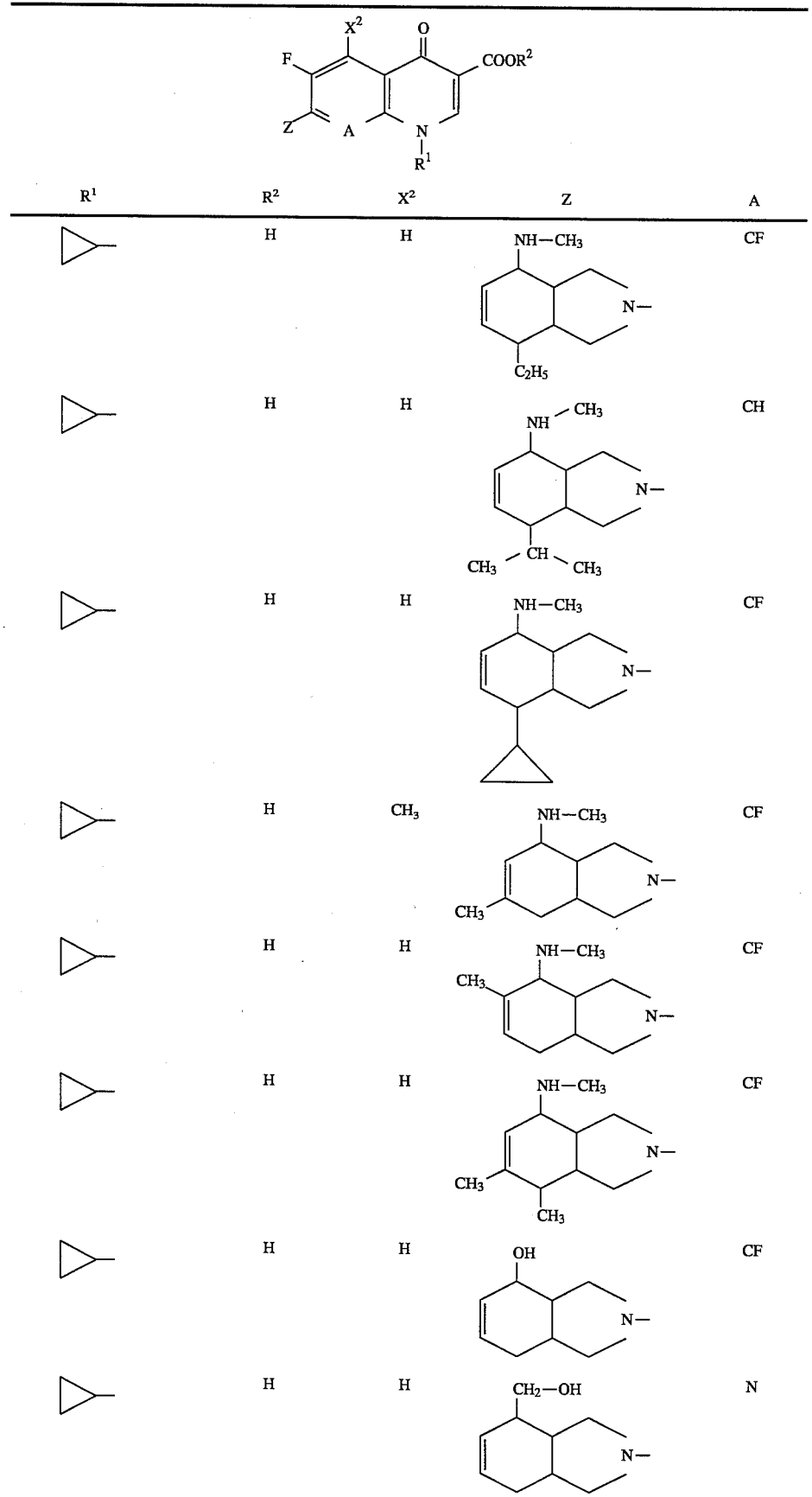

-continued
| R¹ | R² | X² | Z | A |
|---|---|---|---|---|
|  | H | H | 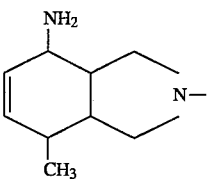 | N |
|  | H | H | 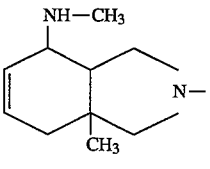 | CF |
|  | —C$_2$H$_5$ | H | 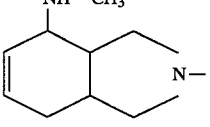 | CCl |
|  | —CH$_2$CH$_2$—OH | H | 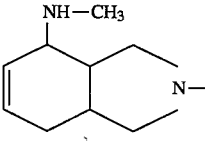 | CCl |
|  | —CH$_2$CH$_2$—NH$_2$ | H | 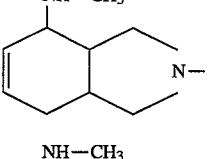 | CCl |
|  | —CH$_2$CH$_2$—NH—CH$_3$ | H | 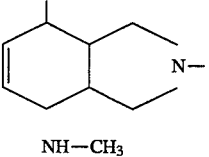 | CCl |
|  | —CH$_2$CH$_2$N(CH$_3$)$_2$ | H | 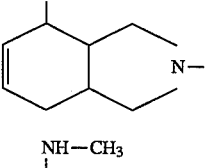 | CCl |
| F—CH$_2$CH$_2$— | H | H | 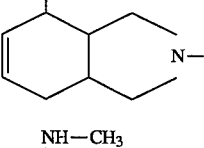 | CF |
| CH$_3$—NH— | H | H | 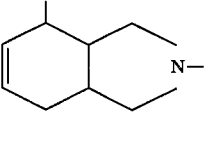 | CF |

-continued

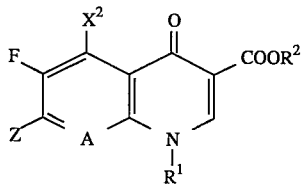

| R¹ | R² | X² | Z | A |
|---|---|---|---|---|
| 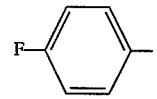 | H | H | 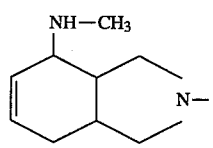 | CF |

The compounds according to the invention have a potent antibiotic action and show, combined with a low toxicity, a broad antibacterial spectrum against Gram-positive and Gram-negative germs, in particular against enterobacteria; above all also against those which are resistant to various antibiotics, such as, for example, penicillins, cephalosporins, aminoglycosides, sulphonamides and tetracyclines.

These useful properties facilitate their use as chemotherapeutic active compounds in medicine and also as substances for the preservation of inorganic and organic materials, in particular of organic materials of all types, for example polymers, lubricants, colours, fibres, leather, paper and wood, and of foodstuffs and water.

The compounds according to the invention are active against a very broad spectrum of microorganisms. Gram-negative and Gram-positive bacteria and bacteria-like organisms can be controlled with their aid, and the diseases caused by these pathogens can also be prevented, alleviated and/or cured.

The compounds according to the invention are distinguished by an intensified action against dormant and resistant germs. In the case of dormant bacteria, that is to say bacteria which show no detectable growth, the compounds have an action at concentrations far below those of previously known substances. This relates not only to the amount to be employed but also to the speed of the destruction. It has been possible to observe such results on Gram-positive and -negative bacteria, in particular in *Staphylococcus aureus, Pseudomonas aeruginosa, Enterococcus faecalis* and *Escherichia coli*.

The compounds according to the invention also exhibit surprising increases in action against bacteria which are classified as less sensitive to comparable substances, in particular resistant *Staphylococcus aureus, Escherichia coli, Pseudomonas aeruginosa* and *Enterococcus faecalis*.

The compounds according to the invention are particularly active against bacteria and bacteria-like microorganisms. They are therefore particularly suitable in human and veterinary medicine for the prophylaxis and chemotherapy of local and systemic infections caused by these pathogens.

The compounds are furthermore suitable for combating protozoonoses and helminthoses.

The compounds according to the invention can be used in various pharmaceutical formulations. Preferred pharmaceutical formulations which may be mentioned are tablets, coated tablets, capsules, pills, granules, suppositories, solutions, suspensions and emulsions, pastes, ointments, gels, creams, lotions, powders and sprays.

The minimum inhibitory concentrations (MIC) were determined by series dilution methods on Iso-Sensitest agar (Oxoid). A series of agar plates each containing active compound concentrations decreasing by twofold dilution each time were prepared for each test substance. The agar plates were inoculated with a Multipoint inoculator (Denley). Overnight cultures of the pathogens, which were first diluted so that each inoculum spot contained about $10^4$ colony-forming particles, were used for the inoculation. The inoculated agar plates were incubated at 37° C. and the germ growth was read off after about 20 hours. The MIC value (μg/ml) indicates the lowest active compound concentration at which no growth was to be detected with the naked eye.

The MIC values of some of the compounds according to the invention are shown in the following table in comparison with 7-(4-amino-1,3-dihydro-isoindol-2-yl)-1-cyclopropyl-6,8-difluoro-1,4 -dihydro-4-oxo-3-quinolinecarboxylic acid (EP 343,560, Example 2).

TABLE

| Test strain: | Example | 1 | 2 | 3 | 4 | 5 | 6 | 7 | 8 | 9 B | 10 | 11 B | Ref*) |
|---|---|---|---|---|---|---|---|---|---|---|---|---|---|
| E. coli | Neumann | 0,02 | 0,03 | 0,02 | 0,13 | 0,06 | 0,03 | 0,03 | 0,13 | 0,02 | 0,06 | 0,25 | 0,5 |
|  | 455/7 | 0,5 | 2 | 0,25 | 16 | 2 | 1 | 0,5 | 2 | 0,5 | 8 | 16 | 128 |
| *Klebsiella* sp. | 8085 | 0,06 | 0,13 | 0,03 | 0,25 | 0,06 | 0,06 | 0,06 | 0,25 | 0,03 | 0,13 | 0,5 | 4 |
| *Morganella morg.* | 932 | 0,06 | 0,13 | 0,03 | 0,5 | 0,06 | 0,06 | 0,03 | 0,25 | 0,06 | 0,25 | 0,5 | 1 |
| *Providencia* spp. | 12012 | 0,06 | 0,13 | 0,03 | 0,25 | 0,13 | 0,13 | 0,06 | 0,5 | 0,06 | 0,25 | 0,5 | 1 |
| *Staphyloccus aureus* | 1756 | 0,02 | 0,02 | 0,02 | 0,03 | 0,02 | 0,02 | 0,02 | 0,03 | 0,03 | 0,06 | 0,06 | 0,03 |
|  | 133 | 0,02 | 0,02 | 0,02 | 0,03 | 0,02 | 0,02 | 0,02 | 0,03 | 0,03 | 0,06 | 0,06 | 0,03 |

| | | MIC values | | | | | | | | | | | |
|---|---|---|---|---|---|---|---|---|---|---|---|---|---|
| Test strain: | Example | 1 | 2 | 3 | 4 | 5 | 6 | 7 | 8 | 9 B | 10 | 11 B | Ref*) |
| Enterocococus | 27101 | 0,03 | 0,06 | 0,02 | 0,13 | 0,03 | 0,06 | 0,02 | 0,13 | 0,03 | 0,25 | 0,25 | 0.5 |
| faecalis | 9790 | 0,03 | 0,06 | 0,02 | 0,13 | 0,03 | 0,06 | 0,02 | 0,13 | 0,02 | 0,25 | 0,25 | 1 |
| Pseudomonas aeruginasa | Walter | 1 | 2 | 0,5 | 16 | 2 | 2 | 1 | 4 | 1 | 4 | 8 | 128 |

*)Reference compound:
7-(4-Amino-1,3-dihydro-isoindol-2-yl)-1-cyclopropyl-6,8-difluoro-1,4-dihydro-4-oxo-3-quinolinecarboxylic acid (EP 343,560, Example 2)

Preparation of the intermediate products:

EXAMPLE A

4-Methylamino-1,3,3a,4,7,7a-hexahydroisoindole

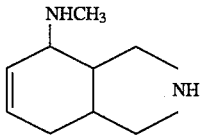

Method I:

14.4 g (60 mmol) of 70% strength 1-(tert.-butyloxycarbonylamino)-1,3-butadiene [J. Org. Chem. 43, 2164 (1978)], as a solution in 30 ml of absolute tetrahydrofuran, are added dropwise to 10.1 g (60 mmol) of N-trimethylsilylmaleimide [J. Org. Chem. 40, 24 (1975)] in 30 ml of absolute tetrahydrofuran, which have been initially introduced into the reaction vessel. When the exothermic reaction has subsided, the mixture is boiled under reflux cooling for a further hour.

The cooled reaction mixture is then added dropwise, under nitrogen, to 7.6 g (0.2 mol) of lithium aluminium hydride in 200 ml of absolute tetrahydrofuran, which have been initially introduced into the reaction vessel. The mixture is then boiled under reflux cooling for 14 hours. 7.6 g of water in 23 ml of tetrahydrofuran, 7.6 g of 10% strength sodium hydroxide solution and 22.8 g of water are then added dropwise in succession to the cooled reaction mixture. The salts are filtered off and the filtrate is concentrated in vacuo. The residue (10.3 g) is distilled at 87° C./0.8 mbar.

The distillate is taken up in 80 ml of absolute pentane, the mixture is filtered and the product is crystallised by cooling to −70° C.

Yield: 3.3 g, melting point: 72°–82° C.

Treatment with an equimolar amount of 2N hydrochloric acid gives 4-methylamino-1,3,3a,4,7,7a-hexahydro-isoindole dihydrochloride of melting point 265°–268° C. (from methanol).

Method II:

a) 4-(tert.-Butyloxycarbonylamino)-1,3-dioxo-1,3,3a,4,7,7a-hexahydroisoindole 48.0 g (0.5 mol) of maleimide are initially introduced into the reaction vessel as a solution in 200 ml of absolute tetrahydrofuran, and 120 g (0.5 mol) of approximately 70% strength 1-(tert.-butyloxycarbonylamino)-1,3-butadiene are added dropwise as a solution in 500 ml of absolute tetrahydrofuran, the temperature being kept at 20° to 30° C. The mixture is subsequently stirred overnight at room temperature. It is then concentrated and the residue is recrystallised from ethyl acetate. 57 g of product having a melting point of 177° to 182° C. are obtained. A further 13 g of melting point 158° to 160° C. are obtained from the mother liquor.

b) 4-Methylamino-1,3,3a,4,7,7a-hexahydroisoindole 27.1 g (0.71 mol) of lithium aluminium hydride in 300 ml of absolute tetrahydrofuran are initially introduced into the reaction vessel, under nitrogen, and a solution of 57 g (0.21 mol) of 4-(tert.-butyloxycarbonylamino)-1,3-dioxo-1,3,3a,4,7,7a-hexahydroisoindole in 570 ml of absolute tetrahydrofuran is added dropwise. The mixture is then boiled under reflux cooling overnight. After cooling, 27.1 g of water in 82 ml of tetrahydrofuran, 27.1 g of 10% strength sodium hydroxide solution and 81.3 g of water are added dropwise to the batch in succession. The salts are filtered off with suction and washed with tetrahydrofuran and the filtrate is concentrated in vacuo. The residue is distilled under a high vacuum.

Yield: 19.1 g

EXAMPLE B

4-Amino-1,3,3a,4,7,7a-hexahydro-isoindole

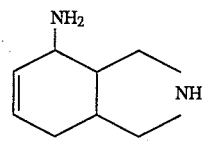

13.3 g (50 mmol) of 4-tert.-butyloxycarbonylamino-1,3-dioxo-1,3,3a,4,7,7a-hexahydro-isoindole (from Example A, method II) are stirred in 166 ml of trifluoroacetic acid at room temperature overnight. The trifluoroacetic acid is then distilled off under 10 mbar and the residue is freed from residues of acid at 50° under a high vacuum. It is then taken up in absolute tetrahydrofuran and the mixture is concentrated in vacuo. The residue is taken up in 100 ml of absolute tetrahydrofuran and the mixture is added dropwise to a solution of 11.3 g (0.3 mol) of lithium aluminium hydride in 300 ml of absolute tetrahydrofuran, under nitrogen. The mixture is then boiled under reflux cooling for 16 hours. After cooling, 11.3 g of water in 34 ml of tetrahydrofuran, 11.3 ml of 10% strength sodium hydroxide solution and 34 ml of water are added dropwise in succession. The precipitate is filtered off with suction and washed with tetrahydrofuran. The filtrate is concentrated and the residue is distilled.

Yield: 2.2 g, content: 92% (determined by gas chromatography)

Boiling point: 70°/0.2 mbar

EXAMPLE C

7-Methyl-4-methylamino-1,3,3a,4,7,7a-hexahydro-isoindole

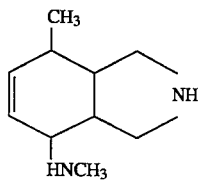

Analogously to Example A, method I, 21.9 g (0.12 mol) of 1-(tert.-butyloxycarbonylamino)-1,3-pentadiene are reacted with 20.3 g (0.12 mol) of N-trimethylsilylmaleimide and the product is then reduced with 15.2 g (0.4 mol) of lithium aluminiumhydride. The crude product is recrystallised from tetrahydrofuran.

Yield: 6.2 g, melting point: 106°–108° C.

EXAMPLE D

5-Bromo-1-cyclopropyl-6,7,8-trifluoro-1,4-dihydro-4-oxo-3-quinolinecarboxylic acid

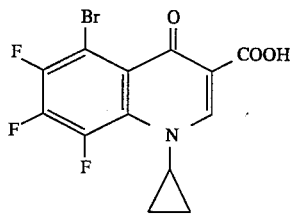

a) 2-Bromo-3,4,5,6-tetrafluoro-benzoyl chloride 365 g (1.33 mol) of 2-bromo-3,4,5,6-tetrafluorobenzoic acid [Tetrahedron 2.3, 4719 (1967)] are introduced into 2 l of thionyl chloride and the mixture is heated under reflux for 11 hours until the evolution of gas stops. Excess thionyl chloride is stripped off in vacuo and the residue is distilled.

Yield: 330 g (85% of theory)

Boiling point: 81°–85° C./3–5 mbar b) Diethyl (2-bromo-3,4,5,6-tetrafluoro-benzoyl)malonate 15.9 g (0.167 mol) of magnesium chloride in 150 ml of anhydrous acetonitrile (dried over zeolite) are initially introduced into the reaction vessel and 26.9 g (0.167 mol) of diethyl malonate are added dropwise, while cooling. The mixture is cooled to 0° C., 46 ml (33.7 g=0.33 mol) of triethylamine are added dropwise and the mixture is subsequently stirred for 30 minutes. 48.9 g (0.168 mol) of 2-bromo-3,4,5,6-tetrafluorobenzoyl chloride are then added dropwise and the mixture is subsequently stirred at 0° C. for a further hour and brought to room temperature overnight. 100 ml of 5N hydrochloric acid are added, the mixture is extracted three times with methylene chloride and the extract is dried with $Na_2SO_4$ and concentrated in vacuo.

Crude yield: 62.7 g c) Ethyl (2-bromo-3,4,5,6-tetrafluoro-benzoyl)-acetate 60 g of crude diethyl (2-bromo-3,4,5,6-tetrafluorobenzoyl)-malonate are introduced into 150 ml of water, 0.6 g of 4-toluenesulphonic acid are added and the mixture is heated under reflux for 6 hours. It is extracted with methylene chloride and the extract is washed with water, dried with $Na_2SO_4$ and concentrated.

Crude yield: 46 g

Boiling point (distillation of a sample in a bulb tube): 150°–160° C. (oven)/3 mbar;

Mass spectrum: m/e 342 ($M^+$), 297 ($M^+$—$OC_2H_5$), 263 ($M^+$—Br), 257, 255 (M+—$CH_2CO_2C_2H_5$), 235 (263–28).

d) Ethyl 2-(2-bromo-3,4,5,6-tetrafluoro-benzoyl)-3-ethoxyacrylate 45 g of crude ethyl (2-bromo-3,4,5,6-tetrafluorobenzoyl)-acetate are introduced into 32.2 g (0.31 mol) of acetic anhydride and 28.4 g (0.19 mol) of triethyl orthoformate and the mixture is heated under reflux for 2 hours. Excess reagent is stripped off, first in vacuo and then under a high vacuum (bath up to 120°–130° C.), and the crude product is reacted for the next stage.

Crude yield: 50.7 g e) Ethyl 2-(2-bromo-3,4,5,6-tetrafluoro-benzoyl)-3-cyclopropylamino-acrylate 8.6 g (0.15 mol) of cyclopropylamine are added dropwise to 50.7 g of crude product from stage d) in 90 ml of ethanol, while cooling with ice, the mixture is subsequently stirred at room temperature, left to stand overnight and cooled thoroughly again, and the crystals are filtered off with suction, washed with cold ethanol and dried.

Yield: 29 g (42% over 4 stages)

Melting point: 103°–105° C. (from ethanol)

f) Ethyl 5-bromo-1-cyclopropyl-6,7,8-trifluoro-1,4-dihydro-4-oxo-3-quinolinecarboxylate 28 g (68 mmol) of ethyl 2-(2-bromo-3,4,5,6-tetrafluoro-benzoyl)-3-cyclopropylamino-acrylate are heated under reflux in 88 ml of dimethylformamide with 6.9 g (164 mmol) of sodium fluoride for 6 hours. After cooling, the mixture is poured into water and the precipitate (red) which has separated out is filtered off with suction, washed with a large quantity of water and dried at 80° C. in a circulating air cabinet.

Crude yield: 27.3 g

Melting point: 150°–175° C.; after recrystallisation from glycol monomethyl ether: melting point: 187°–191° C.

g) 5-Bromo-1-cyclopropyl-6,7,8-trifluoro-1,4-dihydro-4-oxo-3-quinolinecarboxylic acid 26.7 g (68 mmol) of crude ethyl 5-bromo-1-cyclopropyl-6,7,8-trifluoro-1,4-dihydro-4-oxo-3-quinolinecarboxylate are introduced into a mixture of 165 ml of acetic acid, 110 ml of water and 18 ml of concentrated sulphuric acid and the mixture is heated under reflux for 2 hours. The cooled reaction mixture is poured onto ice-water and the precipitate which has separated out is filtered off with suction, rinsed with a large quantity of water and dried in a circulating air cabinet at 80° C.

Yield: 19.7 g (80% of theory)

Melting point: 208°–210° C. (with decomposition); after recrystallisation from glycol monomethyl ether:

melting point: 212°–214° C. (with decomposition)

$^1$H-NMR (DMSO): 8.73 s (1H on C-2), 4.16 m (1H, cyclopropyl), 1.2 m (4H, cyclopropyl) [ppm].

Mass spectrum: m/e 361 ($M^+$), 343 ($M^+$—$H_2O$), 317 (M—$CO_2$), 41 (100%, $C_3H_5$).

EXAMPLE E

5-Bromo-1-(2,4-difluorophenyl)-6,7,8-trifluoro-1,4-dihydro-4-oxo-3-quinolinecarboxylic acid

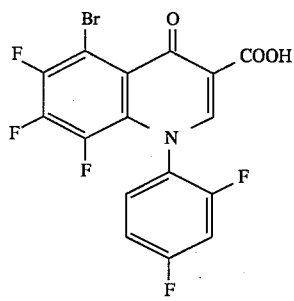

Analogously to Examples De, Df and Dg, the following are obtained with 2,4-difluoroaniline:

a) ethyl 2-(2-bromo-2,3,4,5-tetrafluoro-benzoyl)-3-(2,4-difluorophenylamino)-acrylate, melting point: 116°–117° C., b) ethyl 5-bromo-1-(2,4-difluorophenyl)-6,7,8-trifluoro-1,4-dihydro-4-oxo-3-quinolinecarboxylate, melting point: 190°–192° C. (with decomposition) and c) 5-bromo-1-(2,4-difluorophenyl)-6,7,8-trifluoro-1,4-dihydro-4-oxo-3-quinolinecarboxylic acid, melting point: 237°–240° C. (with decomposition).

Mass spectrum: m/e 433 ($M^+$), 389 (100%, $M^+—CO_2$).

EXAMPLE F 5,8-Dichloro-1-cyclopropyl-6,7-difluoro-1,4-dihydro-4-oxo-3-quinolinecarboxylic acid

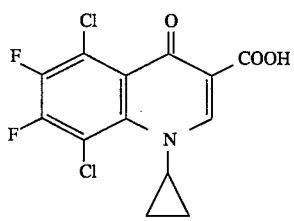

a) 3-Chloro-2,4,5-trifluoro-6-nitrobenzoic acid 210.5 g (1 mol) of 3-chloro-2,4,5-trifluorobenzoic acid (DE 3,420,796) are initially introduced into the reaction vessel in 1000 ml of concentrated sulphuric acid and the mixture is heated to 40° C. 189 g (3 mol) of anhydrous nitric acid are added dropwise, during which the internal temperature is kept between 35° and 45° C. When the addition is complete, the mixture is stirred at room temperature for a further 24 hours. The suspension is poured onto 2 kg of ice. The solid which has precipitated is filtered off with suction, washed with water and dried over KOH in a desiccator.

Yield: 157.5 g (62% of theory)

Melting point: 160°–162° C. (from chlorobenzene)

b) 2-Amino-5-chloro-3,4,6-trifluorobenzoic acid 63.9 g (0.25 mol) of 3-chloro-2,4,5-trifluoro-6-nitrobenzoic acid and 15 g of Raney nickel are suspended in 450 ml of ethanol. Hydrogenation is carried out at 10°–15° C. under a hydrogen pressure of 5–10 bar until the uptake of hydrogen has ended. The crude reaction mixture is poured onto 1 l of water. The carboxylic acid which has precipitated is dissolved by addition of 10% strength sodium hydroxide solution. When the catalyst has been filtered off with suction, a pH of 2–3 is established by addition of half-concentrated hydrochloric acid. The precipitate is filtered off with suction, washed with water and dried over KOH in a desiccator.

Yield: 51.8 g (92% of theory)

Melting point: 183°–185° C.

c) 2,5-Dichloro-3,4,6-trifluorobenzoic acid 45.1 g (0.2 mol) of 2-amino-5-chloro-3,4,6-trifluorobenzoic acid are initially introduced into the reaction vessel in 300 ml of anhydrous acetic acid. 27.9 g (0.22 mol) of nitrosylsulphuric acid, dissolved in 150 ml of concentrated sulphuric acid, are added dropwise at an internal temperature of 25°–30° C. The mixture is then stirred at room temperature for 1 hour. A solution of amidosulphonic acid which is saturated at room temperature is added dropwise until the evolution of nitrogen has ended, in order to remove the excess nitrite.

10 g (0.1 mol) of copper(I) chloride are initially introduced into the reaction vessel in 300 ml of half-concentrated hydrochloric acid. The solution of the diazonium salt prepared as described above is added dropwise at an internal temperature of 10°–15° C. The mixture is then stirred at room temperature for a further 2 hours. The crystals which have precipitated are washed with water and dried over KOH in a desiccator.

Yield: 26.8 g (55% of theory)

Melting point: 119°–120° C.

d) 2,5-Dichloro-3,4,6-trifluorobenzoyl chloride 160 ml of thionyl chloride are initially introduced into the reaction vessel at room temperature. 36.8 g (0.15 mol) of 2,5-dichloro-3,4,6-trifluorobenzoic acid are added in portions, while stirring. After addition of 0.5 ml of dimethylformamide, the mixture is slowly heated to 80°–90° C. and is stirred at this temperature for 5 hours. It is then concentrated and the residue is distilled under a high vacuum.

Yield: 31.6 g (80% of theory)

Boiling point: 65° C./1.4 mbar e) Ethyl (2,5-dichloro-3,4,6-trifluorobenzoyl)-acetate 30.6 g (0.15 mol) of ethyl trimethylsilyl malonate are initially introduced into the reaction vessel in 100 ml of diethyl ether. 60 ml of a 2.5M solution of n-butyllithium (0.15 mol) are added dropwise at –78° C. When the addition is complete, the mixture is stirred at this temperature for a further 10 minutes. 26.4 g (0.1 mol) of 2,5-dichloro-3,4,6-trifluorobenzoyl chloride, dissolved in 100 ml of dimethoxyethane, are then added dropwise.

When the addition is complete, the mixture is allowed to come to room temperature and is stirred at this temperature for 20 hours. 100 ml of water are then added dropwise and the organic phase is separated off, dried with sodium sulphate and concentrated. The residue is taken up in 200 ml of petroleum ether and the mixture is filtered with suction. The solid which has been filtered off with suction is discarded. The filtrate is concentrated and the residue is distilled under a high vacuum.

Yield: 21.3 g (68% of theory)

Boiling point: 115°–120° C./0.8 mbar f) Ethyl 2-(2,5-dichloro-3,4,6-trifluorobenzoyl)-3-ethoxyacrylate A mixture of 31.5 g (0.1 mol) of ethyl (2,5-dichloro-3,4, 6-trifluorobenzoyl)-acetate, 22.2 g (0.15 mol) of triethyl orthoformate and 25.5 g (0.25 mol) of acetic anhydride is heated under reflux for 2 hours (heating bath temperature of 150° C.). Low-boiling constituents are distilled off first under a waterpump vacuum and then under a high vacuum up to a bottom temperature of 130° C. The residue is used further as crude product.

Yield: 34.7 g (94% of theory)

g) Ethyl 2-(2,5-dichloro-3,4,6-trifluorobenzoyl)-3-cyclopropylaminoacrylate 37.1 g (0.1 mol) of ethyl 2-(2,5-dichloro-3,4,6-trifluorobenzoyl)-3-ethoxyacrylate are initially introduced into the reaction vessel in 100 ml of ethanol. 6.8 g (0.12 mol) of cyclopropylamine, dissolved in 10 ml of ethanol, are added dropwise. The mixture is then stirred at room temperature for 4 hours. The precipitate is filtered off with suction, washed with petroleum ether and dried in air.

Yield: 30.6 g (80% of theory)

Melting point: 113°–115° C.

h) Ethyl 5,8-dichloro-1-cyclopropyl-6,7-difluoro-1,4-dihydro-4-oxo-3-quinolinecarboxylate 19.1 g (0.05 mol) of ethyl 2-(2,5-dichloro-3,4,6-trifluorobenzoyl)-3-cyclopropylamino-acrylate are heated at 160°–170° C. together with 4.2 g (0.1 mol) of sodium fluoride in 100 ml of N-methyl-2-pyrrolidone for 5 hours. After cooling, the mixture is poured onto 200 ml of water. The solid which has precipitated is filtered off with suction, washed with water and dried at 80° C. in a drying cabinet.

Yield: 17.0 g (94% of theory)

Melting point: 185°–186° C.

i) 5,8-Dichloro-1-cyclopropyl-6,7-difluoro-1,4-dihydro-4-oxo-3-quinolinecarboxylic acid 18.1 g (0.05 mol) of ethyl 5,8-dichloro-1-cyclopropyl-6,7-difluoro-1,4 -dihydro-4-oxo-3-quinolinecarboxylate are stirred in a mixture of 360 ml of acetic acid, 300 ml of water and 40 ml of concentrated sulphuric acid at 80° C. for 2.5 hours. After cooling, the crystals which have precipitated are filtered off with suction, washed with water and dried at 80° C. in a drying cabinet.

Yield: 15.7 g (94% of theory)

Melting point: 219°–220° C.

$^1$H-NMR (CDCl$_3$): 8.91 (s, 1H, C2), 4.35 (m, 1H, cyclopropyl-CH), 1.35 and 1.0 ppm (2m, each 2H, cyclopropyl-CH$_2$).

EXAMPLE G 5,8-Dichloro-1-(2,4-difluorophenyl)-6,7-difluoro-1,4-dihydro-4-oxo-3-quinolinecarboxylic acid

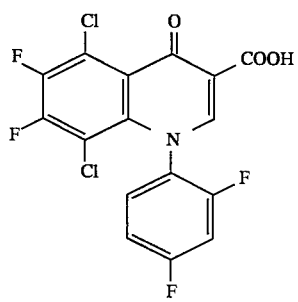

Analogously to Examples Fg, Fh and Fi, the following are obtained with 2,4-difluoroaniline:

a) ethyl 2-(2,5-dichloro-3,4,6-trifluorobenzoyl)-3-(2,4-difluorophenylamino)-acrylate Melting point: 103°–104° C.

b) ethyl 5,8-dichloro-1-(2,4-difluorophenyl)-6,7-difluoro-1,4-dihydro-4-oxo-3-quinolinecarboxylate Melting point: 220°–221° C.

c) 5,8-dichloro-1-(2,4-difluorophenyl)-6,7-difluoro-1,4-dihydro-4-oxo-3-quinolinecarboxylic acid Melting point: 223°–224° C.

EXAMPLE H

7-Isopropyl-4-methylamino-1,3,3a,4,7,7a-hexahydroisoindole

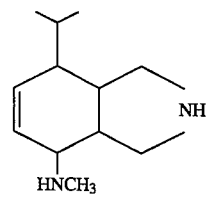

50 g (0.24 mol) of 1-(tert.-butyloxycarbonylamino)-5-methyl-1,3-hexadiene are stirred together with 23 g (0.24 mol) of maleimide in 75 ml of ethanol and 75 ml of water under reflux for 24 hours. After cooling, the solid is filtered off with suction and rinsed with water to give, after drying, 56.3 g (76% of theory) of a solid of melting point 192°–195° C. 15 g (0.049 mol) are stirred together with 11 g (0.29 mol) of lithium aluminium hydride in 300 ml of tetrahydrofuran under reflux for 10 hours. After cooling, the mixture is hydrolysed with 10 ml of water, 10 ml of 10 per cent strength sodium hydroxide solution and finally 30 ml of water. The precipitate is filtered off with suction and rinsed with tetrahydrofuran and the combined filtrates are concentrated to dryness. 8.7 g of a solid are obtained and are purified by crystallisation (petroleum ether-ethyl acetate=1:5).

Yield: 43.5 g (51% of theory), melting point: 76°–81° C.

EXAMPLE I

4-Amino-7-isopropyl-1,3,3a,4,7,7a-hexahydro-isoindole

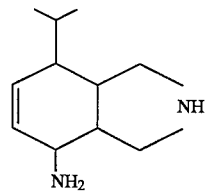

The preparation is carried out analogously to Example B.

$^1$H-NMR (200 MHz, CDCl$_3$): δ=0.95 (6H); 2.3–2.7 (m, 7H); 5.75 (2H).

MS: m/e (% relative intensity): 180 [M$^+$](7); 163 (45); 120 (100); 67 (100).

EXAMPLE J

4-Hydroxymethyl-1,3,3a,4,7,7a-hexahydro-isoindole

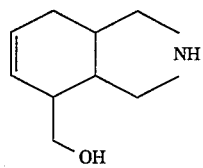

25 g (0.22 mol) of methyl 2,4-pentadienecarboxylate are stirred in 100 ml of dioxane with 20 g (0.21 mol) of maleimide under reflux for 40 hours. The oil (51 g) obtained after concentrating the mixture is stirred in 350 ml of tetrahydrofuran with 20 g (0.52 mol) of lithium aluminium hydride under reflux for 16 hours. After cooling, the mixture is hydrolysed with 63 ml of water, 63 ml of 10 per cent strength sodium hydroxide solution and finally 60 ml of water, and the precipitate is filtered off with suction and rinsed several more times with tetrahydrofuran. The combined filtrates are concentrated and distilled under a high vacuum.

Yield: 10 g (30% of theory)

Boiling point: 96°–115° C./0.07 mbar.

EXAMPLE K

4-Methylaminomethyl-1,3,3a,4,7,7a-hexahydroisoindole

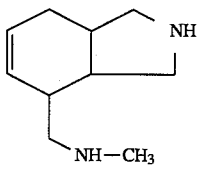

a) 1-tert.-Butyloxycarbonylamino-2,4-pentadiene 1-tert.-Butyloxycarbonylamino-2,4-pentadiene is obtained as a light-coloured oil in a quantitative yield by reaction of 1-amino-2,4-pentadiene (P. A. Grieco et al., Tetrahedron 42, 2847 [1986]) with di-tert.-butyl carbonate in dioxane at room temperature and pH 8–10 for 12 hours.

$^1$H-NMR (200 MHz, CDCl$_3$): δ=1.45 (9H), 3.78 (2H); 4.65 (br., 1H); 5.05°–5.21 (m, 2H); 5.60–5.75 (m, 1H); 6.08–6.42 ppm (m, 2H).

b) 4-tert.-Butyloxycarbonylaminomethyl-1,3-dioxo-1,3,3a,4,7,7a-hexahydro-isoindole

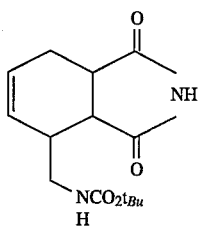

30 g (0.16 mol) of 1-tert.-butyloxycarbonylamino-2,4-pentadiene are stirred together with 16 g (0.16 mol) of maleimide in 120 ml of dioxane under reflux for 12 hours. After cooling, the mixture is concentrated to half and the solid is filtered off with suction.

Yield: 35.3 g (76%)

Melting point: 197.5°–198.5° C.

c) 4-Methylaminomethyl-1,3,3a,4,7,7a-hexahydroisoindole 4-tert.-Butyloxycarbonylaminomethyl-1,3-dioxo-1,3,3a, 4,7,7a-hexahydroisoindole is reduced with lithium aluminium hydride by a method analogous to that described in Example A, method IIb: yellow oil.

Boiling point: 78° C./0,05 mbar.

EXAMPLE L

4-Aminomethyl-1,3,3a,4,7,7a-hexahydro-isoindole

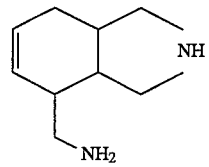

4-tert.-Butyloxycarbonylaminomethyl-1,3-dioxo-1,3,3a, 4,7,7a-hexahydroisoindole is employed in a manner analogous to that described in Example B.

Boiling point: 135°–140° C./0,1 mbar.

EXAMPLE M

6-Methyl-4-methylamino-1,3,3a,4,7,7a-hexahydro-isoindole

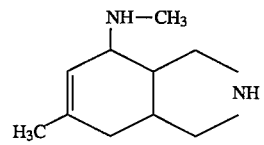

a) 4-(tert.-Butyloxycarbonylamino)-1,3-dioxo-6-methyl-1,3,3a,4,7,7a-hexahydro-isoindole

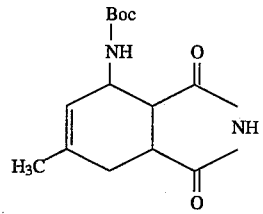

1-tert.-Butyloxycarbonylamino-3-methyl-1,3-butadiene is reacted in dioxane in accordance with Example A/method IIa.

Melting point: 135° C.

b) 6-Methyl-4-methylamino-1,3,3a,4,7,7a-hexahydroisoindole

Analogously to Example B, 5.6 g (20 mmol) of the product from Example Ma) are heated under reflux with 2.2 g (60 mmol) of lithium aluminium hydride in 60 ml of tetrahydrofuran for 15 hours. Working up by distillation gives 1.2 g of the product of boiling point 68°–71° C./0.2–0.3 mbar.

EXAMPLE N

4-Amino-7-methyl-1,3,3a,4,7,7a-hexahydro-isoindole

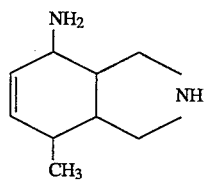

a) 4-(tert.-Butyloxycarbonylamino)-1,3-dioxo-7-methyl-1,3,3a,4,7,7a-hexahydro-isoindole

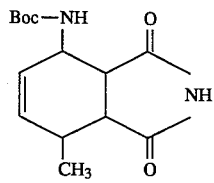

1-tert.-Butyloxycarbonylamino-1,3-pentadiene is employed in accordance with Example A/method IIa and the reaction product is recrystallised from dioxane.

Yield: 79%

Melting point: 208°–211° C.

b) 4-Amino-7-methyl-1,3,3a,4,7,7a-hexahydro-isoindole

The product from Example Na) is employed in accordance with Example B to give the free amine as an oil of boiling point 83°–92° C./0.1 mbar, which crystallises on standing.

Content: 90% pure (according to the gas chromatogram)

EXAMPLE O

4-Amino-7-cyclopropyl-1,3,3a,4,7,7a-hexahydro-isoindole

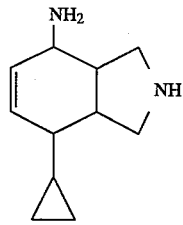

a) 4-(tert.-Butoxycarbonylamino)-7-cyclopropyl-1,3-dioxo-1,3,3a,4,7,7a-hexahydro-isoindole 1-tert.-Butoxycarbonylamino-4-cyclopropyl-1,3-butadiene (prepared in a manner analogous to that described in J. Org. Chem. 43, 2164 [1978]; IR (CCl$_4$): 3300, 1720, 1605 cm$^{-1}$) is reacted in dioxane in accordance with Example A/method II.

Melting point: 195,5°–196,5° C.

b) 4-Amino-7-cyclopropyl- 1,3,3a,4,7,7a-hexahydro-isoindole

Analogously to Example B, the product from Example O a) is reacted with lithium aluminium hydride to give a viscous oil.

FAB-MS (glycerin/dimethylsulfoxide): m/e 179 (M+H$^+$).

Preparation of the active compounds:

EXAMPLE 1

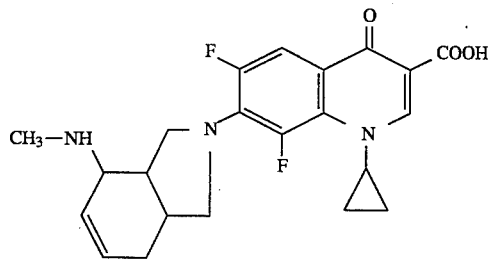

A mixture of 1.42 g (5 mmol) of 1-cyclopropyl-6,7,8-trifluoro-1,4-dihydro-4-oxo-3 -quinolinecarboxylic acid in 10 ml of acetonitrile and 5 ml of dimethylformamide with 560 mg (5 mmol) of 1,4-diazabicyclo[2.2.2]octane, 0.84 g (5.5 mmol) of 4-methylamino-1,3,3a,4,7,7a-hexahydro-isoindole is heated under reflux for 1 hour. The mixture is concentrated, the residue is stirred with 60 ml of water (pH 6–7) and the precipitate which has separated out is filtered off with suction, washed with water and dried at 90° C. under a high vacuum.

Yield: 1.61 g (86.3% of theory) of 1-cyclopropyl-6,8-difluoro-1,4-dihydro-7 -(4-methylamino-1,3,3a,4,7,7a-hexahydro-isoindol-2-yl)-4-oxo-3-quinolinecarboxylic acid, melting point: 233°–235° C. (with decomposition) (from glycol monomethyl ether).

The following are prepared analogously to Example 1:

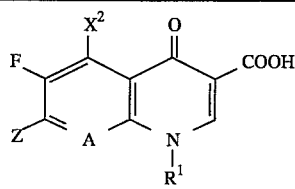

| Example | Z | R¹ | A | $X^2$ | Melting point (with decomposition) [°C.] |
|---|---|---|---|---|---|
| 2 | NH—CH₃ (cyclohexene-isoindoline) | cyclopropyl | CH | H | 216–219 (from glycol monomethyl ether) |
| 3 | " | " | CCl | H | 199–201 |
| 4 | " | " | CH | CH₃ | 198–200 (from glycol monomethyl ether) |
| 5 | NH—CH₃ (cyclohexene-isoindoline) | cyclopropyl | CH | H | 211–214 |
| 6 | " | " | CF | H | 213–217 (from dimethylformamide) |
| 7 | " | C₂H₅— | CCl | H | 139–143 (from glycol monomethyl ether) |
| 8 | (with CH₃, rac.) | C₂H₅— | CF | H | 222–224 (from glycol monomethyl ether) |

EXAMPLE 9

A. 1.5 g (5 mmol) of 8-chloro-1-cyclopropyl-6,7-difluoro-1,4-dihydro-4-oxo-3-quinolinecarboxylic acid are heated under reflux in a mixture of 15 ml of acetonitrile and 7.5 ml of dimethylformamide with 1.2 g (5.3 mmol) of 4-methylamino-1,3,3a,4,7,7a-hexahydro-isoindole dihydrochloride and 1.65 g (15 mmol) of 1,4-diazabicyclo[2.2.2]octane for 1 hour. The suspension is concentrated, the residue is stirred with water and the undissolved residue is filtered off with suction, washed with water and dried at 100° C.

Yield: 1.98 g (92% of theory) of 8-chloro-1-cyclopropyl-6-fluoro-1,4-dihydro-7-(4-methylamino-1,3,3a,4,7,7a-hexahydro-isoindol-2-yl)-4-oxo-3-quinolinecarboxylic acid, melting point: above 198° C. (with decomposition); identical to the product of Example 3.

B. 8.0 g (18.5 mmol) of the product from stage A are suspended in 50 ml of water, 20 ml of 1N hydrochloric acid are added, and the resulting hydrochloride is isolated and dried at 80° C. in vacuo over potassium hydroxide. The crude product (5.9 g) is recrystallised from glycol monomethyl ether.

Yield: 4.4 g (51% of theory) of 8-chloro-1-cyclopropyl-6-fluoro-1,4-dihydro-7-(4-methylamino-1,3,3a,4,7,7a-hexahydro-isoindol-2-yl)-4-oxo-3-quinolinecarboxylic acid hydrochloride Melting point: 248°–253° C. (with decomposition)

EXAMPLE 10

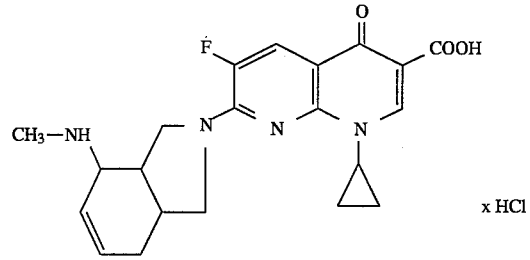

282 mg (1 mmol) of 7-chloro-1-cyclopropyl-6-fluoro-1,4-dihydro-4-oxo-1,8-naphthyridine-3-carboxylic acid are stirred in 3 ml of acetonitrile with 310 mg (2 mmol) of 4-methylamino-1,3,3a,4,7,7a-hexahydro-isoindole at room temperature for 1 hour. The undissolved solid is filtered off with suction, washed with water and acetonitrile and dried at 120° C. under a high vacuum. 0.4 g of 1-cyclopropyl-6-fluoro-1,4-dihydro-7-(4-methylamino-1,3,3a,4,7,7a-hexahydro-isoindol-2-yl)-4-oxo-1,8-naphthyridine-3-carboxylic acid is obtained as a crude product, which is dissolved in 5 ml of half-concentrated hydrochloric acid under the influence of heat. The hydrochloride is precipitated by addition of ethanol, filtered off with suction and dried at 120° C. under a high vacuum.

Yield: 190 mg (44% of theory) of 1-cyclopropyl-6-fluoro-1,4-dihydro-7-(4-methylamino-1,3,3a,4,7,7a-hexahydroisoindol-2-yl)-4-oxo-1,8-naphthyridine-3-carboxylic acid hydrochloride Melting point: 300°–305° C. (with decomposition)

EXAMPLE 11

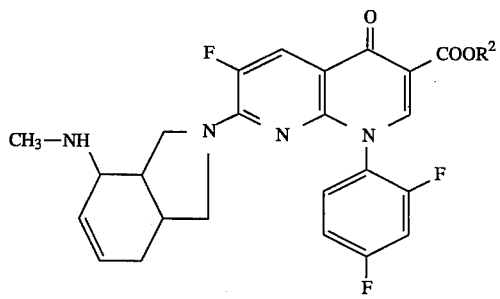

A. R² = C₂H₅
B. R² = H x HCl

A. Method I:

560 mg (5mmol) of 1,4-diazabicyclo[2.2.2]octane and 890 mg (5.3 mmol) of 90% pure 4-methylamino-1,3,3a,4,7,7a-hexahydro-isoindole are added to 1.9 g (5 mmol) of ethyl 7-chloro-1-(2,4-difluorophenyl)-6-fluoro-1,4-dihydro-4-oxo-1,8-naphthyridine-3-carboxylate in 20 ml of acetonitrile. The mixture is stirred at room temperature for 3 hours and then concentrated in vacuo, and the residue is stirred with 80 ml of water. The undissolved residue is filtered off with suction, washed with water and dried.

Yield: 1.6 g (64% of theory) of ethyl 1-(2,4-difluorophenyl)-6-fluoro-1,4-dihydro-7 -(4-methylamino-1,3,3a,4,7,7a-hexahydro-isoindol-2-yl)-4-oxo-1,8-naphthyridine-3-carboxylate, melting point: 173°–176° C. (with decomposition)

Method II:

460 mg (3 mmol) of 1,8-diazabicyclo[5.4.0]undec-7-ene (DBU) and 240 mg (1.1 mmol) of 4-methylamino-1,3,3a,4,7,7a-hexahydroisoindole dihydrochloride are added to 382 mg (1 mmol) of ethyl 7-chloro-1-(2,4 -difluorophenyl)-6-fluoro-1,4-dihydro-4-oxo-1,8-naphthyridine-3-carboxylate in 1 ml of acetonitrile and 1.5 ml of dimethylformamide, and the mixture is stirred at room temperature for 1 hour. It is concentrated in vacuo, 10 ml of water are added and the precipitate which has separated out is filtered off with suction.

Yield: 460 mg (92% of theory) of the ester of melting point 175°–178° C. (with decomposition); identical to the product prepared according to method I.

Mass spectrum: m/e 498 (M⁺), 467 (M⁺-31), 416, 395, 370, 28.

B. 0.47 g (0.9 mmol) of the product from stage A is heated under reflux in a mixture of 4.7 ml of acetic acid and 3.8 ml of half-concentrated hydrochloric acid for 3 hours. The mixture is concentrated to dryness, the residue is stirred with a little ethanol and the undissolved precipitate is filtered off with suction, washed with ethanol and dried at 80° C. under a high vacuum.

Yield: 0.30 g (63% of theory) of 1-(2,4-difluorophenyl)-6-fluoro-1,4-dihydro-7 -(4-methylamino-1,3,3a, 4,7,7a-hexahydro-isoindol-2-yl)-4-oxo-1,8-naphthyridine-3-carboxylic acid hydrochloride melting point: 286°–287° C. (with decomposition).

EXAMPLE 12

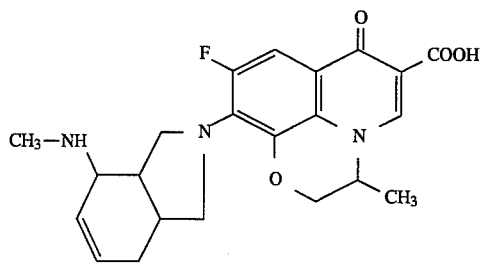

Analogously to Example 1, 9,10-difluoro-2,3-dihydro-3-methyl-7-oxo-7H-pyrido[1,2,3 -de][1,4]benzoxacine-6-carboxylic acid is reacted to give 9-fluoro-2,3-dihydro-3-methyl-10-(4-methylamino-1,3,3 a,4,7,7a-hexahydro-isoindol-2-yl)-7-oxo-7H-pyrido[1,2,3-de][1,4]benzoxacine-6-carboxylic acid of melting point 207°–212° C. (with decomposition).

EXAMPLE 13

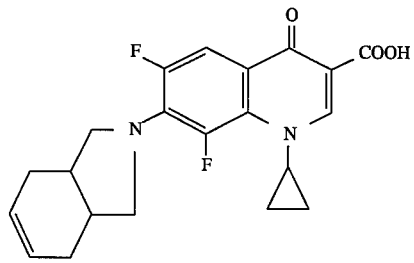

Analogously to Example 1, 1-cyclopropyl-6,8-difluoro-7-(1,3,3a,4,7,7 a-hexahydro-isoindol-2-yl)-1,4-dihydro-4-oxo-3-quinolinecarboxylic acid of melting point 269°–272° C. (with decomposition) is obtained with 1,3,3a,4,7,7a-hexahydro-isoindole [J. Org. Chem. 3.9, 319 (1974)].

EXAMPLE 14

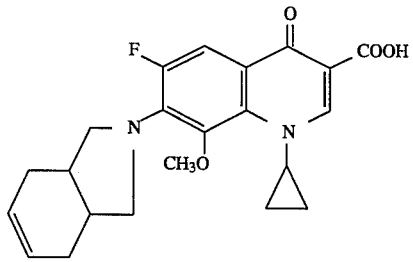

Analogously to Example 13, 1-cyclopropyl-6-fluoro-7-(1, 3,3a,4,7,7a-hexahydro-isoindol-2 -yl)-1,4-difluoro-4-oxo-3-quinolinecarboxylic acid of melting point 229°–231° C. (with decomposition) is obtained with 1-cyclopropyl-6,7-difluoro-1,4-dihydro-8-methoxy-4-oxo-3 -quinolinecarboxylic acid.

Analogously to Example 1, the following compounds are obtained with the products from Examples D and E:

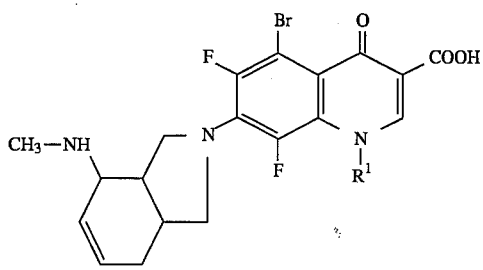

EXAMPLE 15

(R¹=cyclopropyl): 5-bromo-1-cyclopropyl-6,8-difluoro-1,4-dihydro-7-(4 -methylamino-1,3,3a,4,7,7a-hexahydroisoindol-2-yl)-4-oxo-3-quinolinecarboxylic acid, melting point: 208°–211° C. (with decomposition).

EXAMPLE 16

(R¹=2,4-difluorophenyl):5-bromo-1-(2,4-difluorophenyl)-6,8-difluoro-1,4-dihydro-7-(4 -methylamino-1,3,3a,4,7,7a-hexahydro-isoindol-2-yl)-4-oxo-3-quinolinecarboxylic acid.

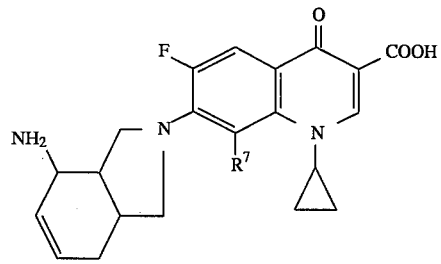

Example 17A: R⁷ = F
Example 17B: R⁷ = FxHCl
Example 18A: R⁷ = Cl
Example 18B: R⁷ = ClxHCl
Example 19: R⁷ = H

EXAMPLE 17

A. Analogously to Example 1, 4-amino-1,3,3a,4,7,7a-hexahydro-isoindole is reacted to give 7-(4-amino-1,3,3a,4,7,7a-hexahydro-isoindol-2-yl)-1 -cyclopropyl-6,8-difluoro-1,4-dihydro-4-oxo-3-quinolinecarboxylic acid of melting point 256°–258° C. (with decomposition).

B. 1.4 g of the betaine from stage A are dissolved in 50 ml of half-concentrated hydrochloric acid at 40° C., the yellow solution is concentrated at 70° C./15 mbar and the crystals are filtered off with suction, washed with ethanol and dried.

Yield: 1.3 g (85% of theory) of 7-(4-amino-1,3,3a,4,7,7a-hexahydro-isoindol-2-yl)-1 -cyclopropyl-6,8-difluoro-1,4-dihydro-4-oxo-3-quinolinecarboxylic acid Melting point: 272°–274° C. (with decomposition).

EXAMPLE 18

A. 7-(4-Amino-1,3,3a,4,7,7a-hexahydro-isoindol-2-yl)-8-chloro-1-cyclopropyl-6-fluoro-1,4-dihydro-4-oxo-3-quinolinecarboxylic acid Melting point: 159°–162° C. (with decomposition).

B. 7-(4-Amino-1,3,3a,4,7,7a-hexahydro-isoindol-2-yl)-8-chloro-1-cyclopropyl-6-fluoro-1,4-dihydro-4-oxo-3-quinolinecarboxylic acid hydrochloride Melting point: 241°–247° C. (with decomposition).

EXAMPLE 19

7-(4-Amino-1,3,3a,4,7,7a-hexahydro-isoindol-2-yl )-1-cyclopropyl-6-fluoro-1,4 -dihydro-4-oxo-3-quinolinecarboxylic acid Melting point: 247°–249° C. (with decomposition) (from dimethylformamide).

EXAMPLE 20

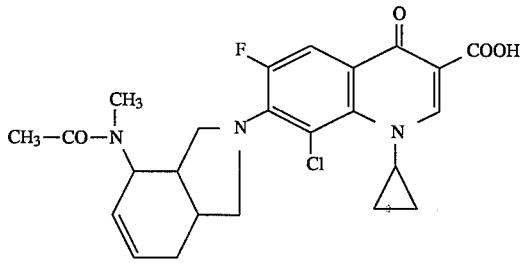

215 mg (0.5 mmol) of the product of Example 3 are dissolved in a mixture of 1.5 ml of dioxane/water (2:1) and 1 ml of 1N sodium hydroxide solution, and 100 mg of acetic anhydride are added and are dissolved at room temperature for 1 hour. The precipitate which has separated out is filtered off with suction, washed with water and dried. Yield: 194 mg (82% of theory) of 7-(N-acetyl-4-methylamino-1,3,3a,4,7,7a-hexahydro-isoindol-2-yl)-8-chloro-1-cyclopropyl-6-fluoro-1,4-dihydro-4-oxo-3-quinolinecarboxylic acid, melting point 217°–218° C. (with decomposition) (from acetonitrile).

EXAMPLE 21

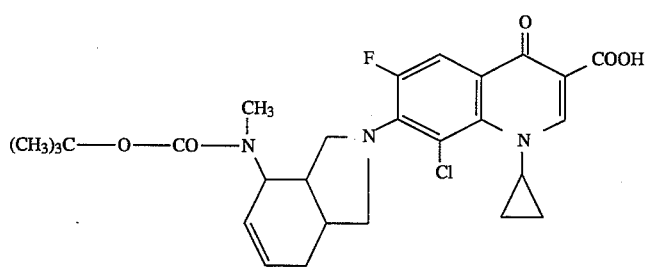

Di-tert.-butyl pyrocarbonate is reacted analogously to Example 20 to give 7-(N-tert.-butoxycarbonyl-4-methylamino-1,3,3a,4,7,7 a-hexahydro-isoindol-2-yl)-8-chloro-1-cyclopropyl-6-fluoro-1,4-dihydro-4-oxo-3-quinolinecarboxylic acid of melting point: 164°–166° C. (with decomposition).

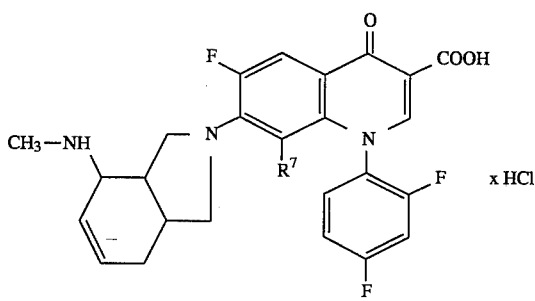

Example 22: $R^7 = H$
Example 23: $R^7 = F$
Example 24: $R^7 = Cl$

EXAMPLE 22

560 mg (5 mmol) of 1,4-diazabicyclo[2.2.2]octane and 0.9 g (6 mmol) of 4-methylamino-1,3,3a,4,7,7a-hexahydroisoindole are added to 1.7 g (5 mmol) of 1-(2,4-difluorophenyl)-6,7-difluoro-1,4 -dihydro-4-oxo-3-quinolinecarboxylic acid in a mixture of 20 ml of acetonitrile and 10 ml of dimethylformamide, and the mixture is stirred at 60°–80° C. for 5 hours. Twice the amount of water is added to the solution and the pH is brought to 7–8 with 1N hydrochloric acid. The mixture is left to stand in a refrigerator for 1 day and the precipitate which has separated out is filtered off with suction, washed with water [crude yield: 2 g, melting point: above 235° C. (with decomposition)] and suspended in a mixture of 2 ml of half-concentrated hydrochloric acid and 7 ml of water for conversion into the hydrochloride. The mixture is heated to about 30°–40° C. and cooled to 0° C., and the salt is filtered off with suction and dried in a desiccator.

Yield: 1.4 g (55% of theory) of 1-(2,4-difluorophenyl)-6-fluoro-1,4-dihydro-7 -(4-methylamino-1,3,3a,4,7,7a-hexahydro-isoindol-2-yl)-4-oxo-3-quinolinecarboxylic acid hydrochloride, melting point: above 285° C. (with decomposition)

EXAMPLE 23

The following compound is obtained analogously to Example 22:

1-(2,4-difluorophenyl)-6,8-difluoro-1,4-dihydro-7-(4-methylamino-1,3,3a,4,7,7 a-hexahydro-isoindol-2-yl)-4-oxo-3-quinolinecarboxylic acid hydrochloride, melting point: above 230° C. (with decomposition)

EXAMPLE 24

The following compound is obtained analogously to Example 22:

8-chloro-1-(2,4-difluorophenyl)-6-fluoro-1,4-dihydro-7-(4-methylamino-1,3,3a,4,7,7 a-hexahydro-isoindol-2-yl)-4-oxo-3-quinolinecarboxylic acid hydrochloride, melting point: above 270° C. (with decomposition)

EXAMPLE 25

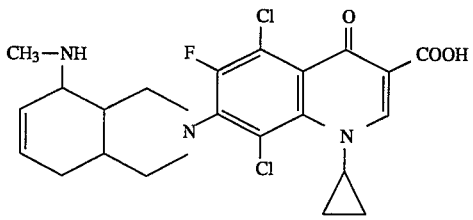

0.67 g (2 mmol) of 5,8-dichloro-1-cyclopropyl-6,7-difluoro-1,4-dihydro-4-oxo-3 -quinolinecarboxylic acid, 0.44 g (4 mmol) of 1,4-diazabicyclo[2.2.2]octane and 0.34 g (2.2 mmol) of 4-methylamino-1,3,3a,4,7,7a-hexahydro-isoindole are stirred in a mixture of 7 ml of acetonitrile and 5 ml of dimethylformamide at 50° C. for 2 hours. After cooling, 20 ml of water are added and the pH is brought to 6–7 with 10% strength hydrochloric acid. After the mixture has been concentrated in vacuo, the residue is boiled up with a mixture of methylene chloride/methanol/water (2:4:1). After cooling, the precipitate is filtered off with suction and dried under a high vacuum at 50° C.

Yield: 0.59 g (63% of theory) of 5,8-dichloro-1-cyclopropyl-6-fluoro-1,4 -dihydro-7-(4-methylamino-1,3,3a,4,7,7a-hexahydro-isoindol-2-yl)-4-oxo-3-quinolinecarboxylic acid melting point: 162°–164° C.

Analogously to Example 1, the following compounds are obtained with the product from Example H:

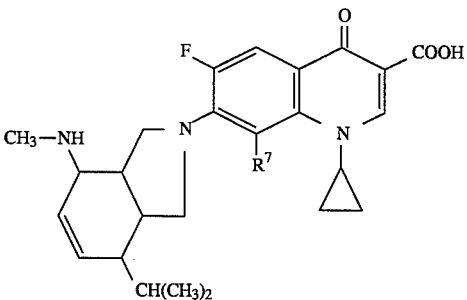

EXAMPLE 26 ($R^7$=F)

1-Cyclopropyl-6,8-difluoro-1,4-dihydro-7-(7-isopropyl-4 -methylamino-1,3,3a,4,7,7a-hexahydro-isoindol-2-yl)-4-oxo-3-quinolinecarboxylic acid of melting point 266°–271° C. (with decomposition) (from glycol monomethyl ether).

EXAMPLE 27 ($R^7$=Cl)

8-Chloro-1-cyclopropyl-6-fluoro-1,4-dihydro-7-(7-isopropyl-4-methylamino-1,3,3 a,4,7,7a-hexahydro-isoindol-2-yl)-4-oxo-3-quinolinecarboxylic acid of melting point 220°–223° C. (with decomposition) (from dimethylformamide).

Analogously to Example 1, the following compounds are obtained with the product from Example I:

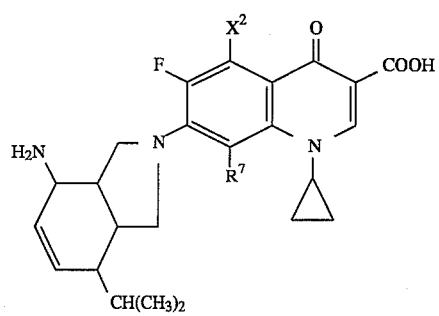

EXAMPLE 28 ($X^2$=H, $R^7$=F)

7-(4-Amino-7-isopropyl-1,3,3a,4,7,7a-hexahydro-isoindol-2-yl)-1-cyclopropyl-6,8-difluoro-1,4-dihydro-4-oxo-3-quinolinecarboxylic acid of melting point 209°–211° C. (with decomposition).

EXAMPLE 29 ($X^2$=$CH_3$, $R^7$=H)

7-(4-Amino-7-isopropyl-1,3,3a,4,7,7a-hexahydro-isoindol-2-yl)-1-cyclopropyl-6-fluoro-1,4-dihydro-5-methyl-4-oxo-3-quinolinecarboxylic acid of melting point 274° to 275° C. (with decomposition). MS: m/e 439 ($M^+$)

Analogously to Example 1, the following compounds are obtained with the compounds from Examples J, K or L:

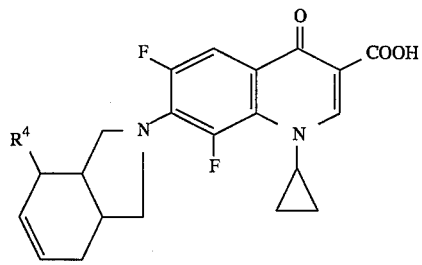

EXAMPLE 30 ($R^4$=$CH_2$—OH)

1-Cyclopropyl-6,8-difluoro-1,4-dihydro-7-(4-hydroxymethyl-1,3,3a,4,7,7 a-hexahydro-isoindol-2-yl)-4-oxo-3-quinolinecarboxylic acid of melting point 254°–255° C. (with decomposition) (from dimethylformamide).

EXAMPLE 31 ($R^4$=$CH_2$—NH—$CH_3$)

1-Cyclopropyl-6,8-difluoro-1,4-dihydro-7-(4-methylaminomethyl-1,3,3a,4,7,7 a-hexahydro-isoindol-2-yl)-4-oxo-3-quinolinecarboxylic acid of melting point 242°–244° C. (with decomposition).

EXAMPLE 32 ($R^4$=$CH_2$—$NH_2$)

7-(4-Aminomethyl-1,3,3a,4,7,7a-hexahydro-isoindol-2-yl)-1-cyclopropyl-6,8-difluoro-1,4-dihydro-4-oxo-3-quinolinecarboxylic acid.

Analogously to Example 1, the following compounds are obtained with the compound from Example M:

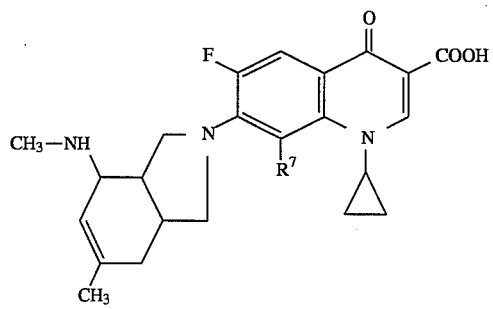

EXAMPLE 33 ($R^7$=F)

1-Cyclopropyl-6,8-difluoro-1,4-dihydro-7-(6-methyl-4-methylamino-1,3,3a,4,7,7 a-hexahydro-isoindol-2-yl)-4-oxo-3-quinolinecarboxylic acid of melting point 223°–224° C. (with decomposition) (from glycol monomethyl ether)

EXAMPLE 34 ($R^7$ - Cl)

8-Chloro-1-cyclopropyl-6-fluoro-1,4-dihydro-7-(6-methyl-4-methylamino-1,3,3a,4,7,7 a-hexahydro-isoindol-2-yl)-4-oxo-3-quinolinecarboxylic acid of melting point 198°–200° C. (with decomposition) (from glycol monomethyl ether/dimethylformamide).

Analogously to Example 1, the following compounds are obtained with the compound from Example N:

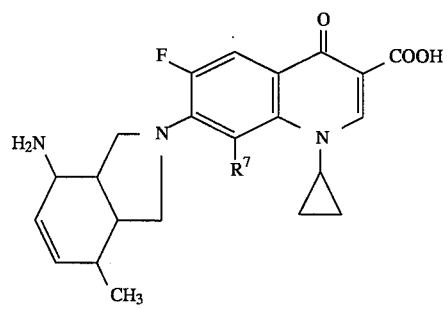

EXAMPLE 35 ($R^7$=F)

7-(4-Amino-7-methyl-1,3,3a,4,7,7a-hexahydro-isoindol-2-yl)-1-cyclopropyl-6,8-difluoro-1,4-dihydro-4-oxo-3-quinolinecarboxylic acid, melting point: 196° to 198° C. (with decomposition) (from glycol monomethyl ether).

EXAMPLE 36 ($R^7$=Cl)

7-(4-Amino-7-methyl-1,3,3a,4,7,7a-hexahydro-isoindol-2-yl)-8-chloro-1-cyclopropyl-6-fluoro-1,4-dihydro-4-oxo-3-quinolinecarboxylic acid, melting point: 124° to 129° C. (with decomposition) (from glycol monomethyl ether).

EXAMPLE 37 (R⁷=H)

7-(4-Amino-7-methyl-1,3,3a,4,7,7a-hexahydro-isoindol-2-yl)-1-cyclopropyl-6-fluoro-1,4-dihydro-4-oxo-3-quinolinecarboxylic acid, melting point: 223° to 225° C. (with decomposition) (from glycol monomethyl ether).

EXAMPLE 38

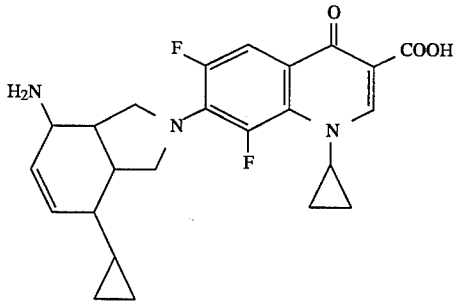

Analogously to Example 1, 7-(4-Amino-7-cyclopropyl-1,3,3a,4,7,7a-hexahydro-isoindol-2-yl)-1-cyclopropyl-6,8-difluoro-1,4-dihydro-4-oxo-3-quinolinecarboxylic acid is obtained with the compound from Example O.

Melting point: 236°–237° C. (with decomposition) (from glycol monomethyl ether).

EXAMPLE 39

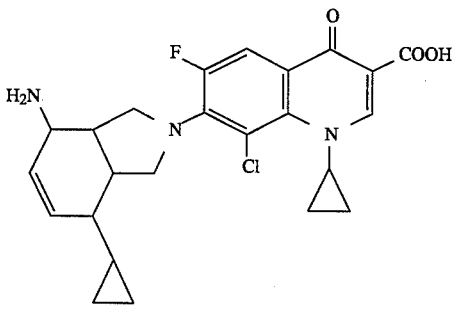

Analogously to Example 1, 7-(4-Amino-7-cyclopropyl-1,3,3a,4,7,7a-hexahydro-isoindol-2-yl)-8-chloro-1-cyclopropyl-6-fluoro-1,4-dihydro-4-oxo-3-quinolinecarboxylic acid is obtained by reaction of 8-chloro-1-cyclopropyl-6,7-difluoro-1,4-dihydro-4-oxo-3-quinolinecarboxylic acid with the compound from Example O.

Melting point: 177°–179° C. (with decomposition) (from glycol monomethyl ether).

We claim:

1. A quinolinecarboxylic acid or ester thereof of the formula

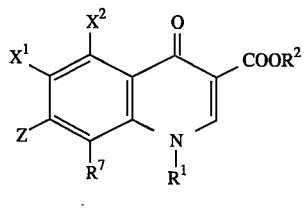

in which $X^1$ is halogen, $X^2$ is hydrogen, amino, alkylamino having 1 to 4 carbon atoms, dialkylamino having 1 to 3 carbon atoms per alkyl group, hydroxyl, alkoxy having 1 to 4 carbon atoms, alkylthio having 1 to 4 carbon atoms, halogen or methyl, $R^1$ is alkyl having 1 to 4 carbon atoms, alkenyl having 2 to 4 carbon atoms, cycloalkyl having 3 to 6 carbon atoms, 2-hydroxyethyl, 2-fluoroethyl, or phenyl which is optionally substituted by 1 or 2 fluorine atoms, $R^2$ is hydrogen, alkyl having 1 to 4 carbon atoms which is optionally substituted by hydroxyl, methoxy, amino, methylamino or dimethylamino, or (5-methyl-2-oxo-1,3-dioxol-4-yl)-methyl, Z is a radical having the structure

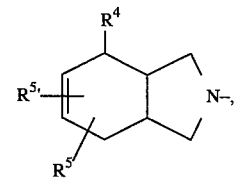

wherein $R^4$ is

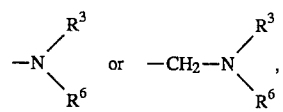

wherein $R^3$ is hydrogen, optionally hydroxyl-substituted $C_1$–$C_3$-alkyl, or alkoxycarbonyl having 1 to 4 C atoms in the alkoxy part and $R^6$ is hydrogen or methyl, $R^5$ is hydrogen, $C_1$–$C_3$-alkyl or cyclopropyl, $R^{5'}$ is hydrogen or methyl, and $R^7$ is H, halogen, methyl, hydroxyl or methoxy, or a pharmaceutically usable hydrate, acid addition salt or alkali metal, alkaline earth metal, silver or guanidinium salt thereof.

2. A compound or hydrate or salt thereof according to claim 1, in which $R^7$ is H, halogen, methyl, hydroxyl or methoxy.

3. A compound or hydrate or salt thereof according to claim 1, in which $X^1$ is fluorine, $X^2$ is hydrogen, amino, methylamino, hydroxyl, methoxy, fluorine, chlorine, bromine or methyl, $R^1$ is alkyl having 1 to 3 carbon atoms, vinyl, cycloalkyl having 3 or 4 carbon atoms, 2-fluoroethyl or phenyl which is optionally substituted by 1 or 2 fluorine atoms, $R^2$ is hydrogen, alkyl having 1 or 2 carbon atoms which is optionally substituted by amino, methylamino or dimethylamino, or (5-methyl-2-oxo-1,3-dioxol-4-yl)-methyl, Z is a radical having the structure

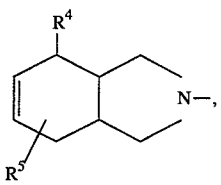

wherein
R⁴ is

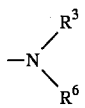

wherein
R³ is hydrogen, optionally hydroxyl-substituted $C_1$–$C_3$-alkyl, or alkoxycarbonyl having 1 to 4 C atoms in the alkoxy part and
R⁶ is hydrogen or methyl,
R⁵ is hydrogen or methyl, and
R⁷ is H, fluorine, chlorine, bromine, methyl or methoxy.

4. A compound or hydrate or salt thereof according to claim 1, in which
X¹ is fluorine,
X² is hydrogen, amino, fluorine, chlorine or bromine,
R¹ is alkyl having 1 or 2 carbon atoms, cyclopropyl or phenyl which is optionally substituted by 1 or 2 fluorine atoms,
R² is hydrogen or alkyl having 1 or 2 carbon atoms and
Z is a radical having the structure

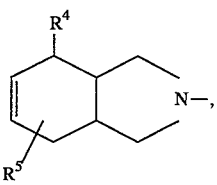

wherein
R⁴ is

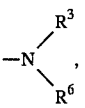

wherein
R³ is hydrogen, methyl, alkoxy-carbonyl having 1 to 4 C atoms in the alkoxy part and
R⁶ is hydrogen or methyl, and
R⁵ is hydrogen or methyl, and
R⁷ is H, fluorine, chlorine or methoxy.

5. A compound or hydrate or salt thereof according to claim 1, selected from the group consisting of
1-Cyclopropyl-6,8-difluoro-1,4-dihydro-7-(4-methylamine-1,3,3 a,4,7,7a-hexahydro-isoindol-2-yl )-4-oxo-3-quinolinecarboxylic acid,
8-Chloro-1-cyclopropyl-6-fluoro-1,4-dihydro-7-(4 methylamino-1,3,3a,4,7,7a-hexahydro-isoindol-2-yl)-4-oxo-3-quinolinecarboxylic acid,
8-Chloro-1-cyclopropyl-6-fluoro-1,4-dihydro-7-(7-methyl-4 -methylamino-1,3,3a,4,7,7a-hexahydro-isoindol-2-yl)-4-oxo-3-quinolinecarboxylic acid,
7-(4-Amino-1,3,3a,4,7,7a-hexahydro-isoindol-2-yl)-1-cyclopropyl-6,8 -difluoro-1,4-dihydro-4-oxo-3-quinolinecarboxylic acid,
7-(4-Amino-1,3,3a,4,7,7a-hexahydro-isoindol-2-yl)-8-chloro-1 -cyclopropyl-6-fluoro-1,4-dihydro-4-oxo-3-quinolinecarboxylic acid, and
7-(4-Amino-1,3,3a,4,7,7a-hexahydro-isoindol-2-yl)-1-cyclopropyl-6 -fluoro-1,4-dihydro-4-oxo-3-quinolinecarboxylic acid.

6. An antibacterial composition comprising an antibacterially effective amount of a compound or addition product thereof according to claim 1 and a diluent.

7. A composition according to claim 6 in the form of a tablet, capsule or ampule.

8. A composition according to claim 6, wherein the diluent comprises an animal feed stock.

9. A method of combating bacteria in a patient in need thereof which comprises administering to such patient an antibacterially effective amount of a compound or addition product thereof according to claim 1.

10. The method according to claim 9, wherein such compound is
1-Cyclopropyl-6,8-difluoro-1,4-dihydro-7-(4-methylamino-1,3,3a,4,7,7 a-hexahydro-isoindol-2-yl)-4-oxo-3-quinolinecarboxylic acid,
8-Chloro-1-cyclopropyl-6-fluoro-1,4-dihydro-7-(4-methylamino-1,3,3a,4,7,7 a-hexahydro-isoindol-2-yl)-4-oxo-3-quinolinecarboxylic acid,
8-Chloro-1-cyclopropyl-6-fluoro-1,4-dihydro-7-(7-methyl-4-methylamino-1,3,3 a,4,7,7a-hexahydro-isoindol-2-yl)-4-oxo-3-quinolinecarboxylic acid,
7-(4-Amino-1,3,3a,4,7,7a-hexahydro-isoindol-2-yl)-1-cyclopropyl-6,8 -difluoro-1,4-dihydro-4-oxo-3-quinolinecarboxylic acid,
7-(4-Amino-1,3,3a,4,7,7a-hexahydro-isoindol-2-yl)-8-chloro-1-cyclopropyl-6 -fluoro-1,4-dihydro-4-oxo-3-quinolinecarboxylic acid,
7-(4-Amino-1,3,3a,4,7,7a-hexahydro-isoindol-2-yl)-1-cyclopropyl-6-fluoro-1,4 dihydro-4-oxo-3-quinolinecarboxylic acid
or an addition product thereof with water or an acid or an alkali salt thereof.

* * * * *

UNITED STATES PATENT AND TRADEMARK OFFICE
CERTIFICATE OF CORRECTION

PATENT NO. : 5,464,796
DATED : November 7, 1995
INVENTOR(S) : Petersen, et al.

It is certified that error appears in the above-indentified patent and that said Letters Patent is hereby corrected as shown below:

On the title page: Item [56]

OTHER PUBLICATIONS: Insert -- Protective Groups in Organic Synthesis, T. W. Green, John Wiley & Sons --

Col. 48, line 5   Delete " methylamine " and substitute -- methylamino --

Signed and Sealed this

Sixteenth Day of April, 1996

Attest:

BRUCE LEHMAN

Attesting Officer

Commissioner of Patents and Trademarks